US005652100A

United States Patent [19]

Hadingham et al.

[11] Patent Number: 5,652,100

[45] Date of Patent: Jul. 29, 1997

[54] STABLY TRANSFECTED RODENT FIBROBLAST CELL LINES EXPRESSING HUMAN GABA-$_A$-RECEPTORS

[75] Inventors: Karen Hadingham, Hertfordshire; Paul John Whiting, Essex, both of United Kingdom

[73] Assignee: Merck Sharpe & Dohme Ltd., England

[21] Appl. No.: 341,610

[22] PCT Filed: Dec. 7, 1993

[86] PCT No.: PCT/GB93/02506

§ 371 Date: Nov. 17, 1994

§ 102(e) Date: Nov. 17, 1994

[87] PCT Pub. No.: WO94/13799

PCT Pub. Date: Jun. 23, 1994

[30] Foreign Application Priority Data

Dec. 10, 1992 [GB] United Kingdom ............... 9225776
Sep. 7, 1993 [GB] United Kingdom ............... 9318528

[51] Int. Cl.$^6$ ........................... C12Q 1/68; G01N 33/53
[52] U.S. Cl. ........................... 435/6; 435/22; 435/64.1; 435/352; 435/357
[58] Field of Search ...................... 435/64.1, 7.2, 435/240.2, 6; 530/350

[56] References Cited

U.S. PATENT DOCUMENTS 5,166,066 11/1992 Carter .................... 435/240.2

FOREIGN PATENT DOCUMENTS

WO92/22652 12/1992 WIPO .

OTHER PUBLICATIONS

S.J. Moss et al., Cloned GABA receptors are maintained in a stable cell line: allosteric and channel properties, European Journal of Pharm., Molec. Pharm., 189: pp. 77–88 (1990).
Pritchett et al, Nature 338:582–585, 13 Apr. 1989.
Wagstaff et al. Am. J. Hum. Genet. 49:330–337, 1991.

Primary Examiner—John Ulm
Attorney, Agent, or Firm—J. Mark Hand; Jack L. Tribble

[57] ABSTRACT

The present invention relates to stably co-transfected eukaryotic cell lines capable of expressing a recombinant GABA$_A$ receptor, particularly a recombinant human GABA$_A$ receptor, which comprises at least one alpha, one beta and one gamma subunit; and to the use of the cell line and/or membrane preparation in selecting compounds and designing medicaments which interact with the respective human recombinant GABA$_A$ receptor.

24 Claims, 20 Drawing Sheets

```
CCTAGCGCTC CTCTCCGGCT TCCACCAGCC CATCGCTCCA CGCTCTCTTG GCTGCTGCAG   60

TCTCGGTCTC TCTCTCTCTC TCTCTCTCTC TCTCTCTCTC TCTCTCTCTC TCTCTCTCTC  120

TCTCTCTCTC TCTCTCCCAA GTTTCCTATC TCGTCAAGAT CAGGGCAAAA GAAGAAAACA  180

CCGAATTCTG CTTGCCGTTT CAGAGCGGCG GTG ATG AAG ACA AAA TTG AAC ATC  234
                                    Met Lys Thr Lys Leu Asn Ile
                                     1               5

TAC AAC ATC GAG TTC CTG CTT TTT GTT TTC TTG GTG TGG GAC CCT GCC   282
Tyr Asn Ile Glu Phe Leu Leu Phe Val Phe Leu Val Trp Asp Pro Ala
            10              15              20

AGG TTG GTG CTG GCT AAC ATC CAA GAA GAT GAG GCT AAA AAT AAC ATT   330
Arg Leu Val Leu Ala Asn Ile Gln Glu Asp Glu Ala Lys Asn Asn Ile
    25              30              35

ACC ATC TTT ACG AGA ATT CTT GAC AGA CTT CTG GAT GGT TAC GAT AAT   378
Thr Ile Phe Thr Arg Ile Leu Asp Arg Leu Leu Asp Gly Tyr Asp Asn
40              45              50              55

CGG CTT AGA CCA GGA CTG GGA GAC AGT ATT ACT GAA GTC TTC ACT AAC   426
Arg Leu Arg Pro Gly Leu Gly Asp Ser Ile Thr Glu Val Phe Thr Asn
                60              65              70

ATC TAC GTG ACC AGT TTT GGC CCT GTC TCA GAT ACA GAT ATG GAA TAT   474
Ile Tyr Val Thr Ser Phe Gly Pro Val Ser Asp Thr Asp Met Glu Tyr
            75              80              85

ACA ATT GAT GTT TTC TTT CGA CAA AAA TGG AAA GAT GAA CGT TTA AAA   522
Thr Ile Asp Val Phe Phe Arg Gln Lys Trp Lys Asp Glu Arg Leu Lys
        90              95              100

TTT AAA GGT CCT ATG AAT ATC CTT CGA CTA AAC AAT TTA ATG GCT AGC   570
Phe Lys Gly Pro Met Asn Ile Leu Arg Leu Asn Asn Leu Met Ala Ser
    105             110             115

AAA ATC TGG ACT CCA GAT ACC TTT TTT CAC AAT GGG AAG AAA TCA GTA   618
Lys Ile Trp Thr Pro Asp Thr Phe Phe His Asn Gly Lys Lys Ser Val
120             125             130             135
```

FIG.2A

```
GCT CAT AAT ATG ACA ATG CCA AAT AAG TTG CTT CGA ATT CAG GAT GAT    666
Ala His Asn Met Thr Met Pro Asn Lys Leu Leu Arg Ile Gln Asp Asp
                140             145             150

GGG ACT CTG CTG TAT ACC ATG AGG CTT ACA GTT CAA GCT GAA TGC CCA    714
Gly Thr Leu Leu Tyr Thr Met Arg Leu Thr Val Gln Ala Glu Cys Pro
            155             160             165

ATG CAC TTG GAG GAT TTC CCA ATG GAT GCT CAT TCA TGT CCT CTG AAA    762
Met His Leu Glu Asp Phe Pro Met Asp Ala His Ser Cys Pro Leu Lys
        170             175             180

TTT GGC AGC TAT GCA TAT ACA ACT TCA GAG GTC ACT TAT ATT TGG ACT    810
Phe Gly Ser Tyr Ala Tyr Thr Thr Ser Glu Val Thr Tyr Ile Trp Thr
    185             190             195

TAC AAT GCA TCT GAT TCA GTA CAG GTT GCT CCT GAT GGC TCT AGG TTA    858
Tyr Asn Ala Ser Asp Ser Val Gln Val Ala Pro Asp Gly Ser Arg Leu
200             205             210             215

AAT CAA TAT GAC CTG CTG GGC CAA TCA ATC GGA AAG GAG ACA ATT AAA    906
Asn Gln Tyr Asp Leu Leu Gly Gln Ser Ile Gly Lys Glu Thr Ile Lys
                220             225             230

TCC AGT ACA GGT GAA TAT ACT GTA ATG ACA GCT CAT TTC CAC CTG AAA    954
Ser Ser Thr Gly Glu Tyr Thr Val Met Thr Ala His Phe His Leu Lys
            235             240             245

AGA AAA ATT GGG TAT TTT GTG ATT CAA ACC TAT CTG CCT TGC ATC ATG   1002
Arg Lys Ile Gly Tyr Phe Val Ile Gln Thr Tyr Leu Pro Cys Ile Met
        250             255             260

ACT GTC ATT CTC TCC CAA GTT TCA TTC TGG CTT AAC AGA GAA TCT GTG   1050
Thr Val Ile Leu Ser Gln Val Ser Phe Trp Leu Asn Arg Glu Ser Val
    265             270             275

CCT GCA AGA ACT GTG TTT GGA GTA ACA ACT GTC CTA ACA ATG ACA ACT   1098
Pro Ala Arg Thr Val Phe Gly Val Thr Thr Val Leu Thr Met Thr Thr
280             285             290             295

CTA AGC ATC AGT GCT CGG AAT TCT CTC CCC AAA GTG GCT TAT GCA ACT   1146
Leu Ser Ile Ser Ala Arg Asn Ser Leu Pro Lys Val Ala Tyr Ala Thr
                300             305             310
```

FIG.2B

```
GCC ATG GAC TGG TTT ATT GCT GTT TGT TAT GCA TTT GTG TTC TCT GCC    1194
Ala Met Asp Trp Phe Ile Ala Val Cys Tyr Ala Phe Val Phe Ser Ala
            315             320             325

CTA ATT GAA TTT GCA ACT GTT AAT TAC TTC ACC AAA AGA GGA TGG ACT    1242
Leu Ile Glu Phe Ala Thr Val Asn Tyr Phe Thr Lys Arg Gly Trp Thr
            330             335             340

TGG GAT GGG AAG AGT GTA GTA AAT GAC AAG AAA AAA GAA AAG GCT TCC    1290
Trp Asp Gly Lys Ser Val Val Asn Asp Lys Lys Lys Glu Lys Ala Ser
            345             350             355

GTT ATG ATA CAG AAC AAC GCT TAT GCA GTG GCT GTT GCC AAT TAT GCC    1338
Val Met Ile Gln Asn Asn Ala Tyr Ala Val Ala Val Ala Asn Tyr Ala
360             365             370             375

CCG AAT CTT TCA AAA GAT CCA GTT CTC TCC ACC ATC TCC AAG AGT GCA    1386
Pro Asn Leu Ser Lys Asp Pro Val Leu Ser Thr Ile Ser Lys Ser Ala
            380             385             390

ACC ACG CCA GAA CCC AAC AAG AAG CCA GAA AAC AAG CCA GCT GAA GCA    1434
Thr Thr Pro Glu Pro Asn Lys Lys Pro Glu Asn Lys Pro Ala Glu Ala
            395             400             405

AAG AAA ACT TTC AAC AGT GTT AGC AAA ATT GAC AGA ATG TCC AGA ATA    1482
Lys Lys Thr Phe Asn Ser Val Ser Lys Ile Asp Arg Met Ser Arg Ile
            410             415             420

GTT TTT CCA GTT TTG TTT GGT ACC TTT AAT TTA GTT TAC TGG GCT ACA    1530
Val Phe Pro Val Leu Phe Gly Thr Phe Asn Leu Val Tyr Trp Ala Thr
            425             430             435

TAT TTA AAC AGA GAA CCT GTA TTA GGG GTC AGT CCT TGAATTGAGA         1576
Tyr Leu Asn Arg Glu Pro Val Leu Gly Val Ser Pro
440             445             450

CCCATGTTAT CTTTGGGATG TATAGCAACA TTAAATTTGG TTTGTTTTGC TATGTACAGT  1636

CTGACTAATA ACTGCTAATT TGTGATCCAA CATGTACAGT ATGTATATAG TGACATAGCT  1696

TACCAGTAGA CCTTTAATGG AGACATGCAT TTGCTAACTC ATGGAACTGC AGACAGAAAG  1756
```

FIG.2C

```
CACTCCATGC GAAAACAGCC ATTGCCTTTT TTAAAGATTT ACCCTAGGAC CTGATTTAAA 1816

GTGAATTTCA AGTGACCTGA TTAATTTCCT ATTCTTCCAA ATGAGATGAA AATGGGGATC 1876

CTGTACAACC CTTTGTGGAC CCTTTTGGTT TAGCTCTTAA GTAGGGGTAT TTTCTACTGT 1936

TGCTTAATTA TGATGGAAGA TAACATTGTC ATTCCTAGAT GAATCCTTTG AAGTAACAAA 1996

CATTGTATCT GACATCAGCT CTGTTCATGA GTGCTCAGAG TCCCTGCTAA TGTAATTGGA 2056

AGCTTGGTAC ACATAAGAAA AACTAGAGAT TTGAAATCTA GCTATGAATT ACTCTATATA 2116

GTATCTATAG CCATGTACAT ATTACAGCAT GACAAGCTCG AAATAATTAT GAGTCAGCCC 2176

GAAAGATGTT AAT                                                  2189
```

FIG.2D

```
GAATTCCCTT GTTTCAGTTC ATTCATCCTT CTCTCCTTTC CGCTCAGACT GTAGAGCTCG  60

GTCTCTCCAA GTTTGTGCCT AAGAAG ATG ATA ATC ACA CAA ACA AGT CAC TGT  113
                            Met Ile Ile Thr Gln Thr Ser His Cys
                              1               5

TAC ATG ACC AGC CTT GGG ATT CTT TTC CTG ATT AAT ATT CTC CCT GGA  161
Tyr Met Thr Ser Leu Gly Ile Leu Phe Leu Ile Asn Ile Leu Pro Gly
 10              15                  20                  25

ACC ACT GGT CAA GGG GAA TCA AGA CGA CAA GAA CCC GGG GAC TTT GTG  209
Thr Thr Gly Gln Gly Glu Ser Arg Arg Gln Glu Pro Gly Asp Phe Val
             30                  35                  40

AAG CAG GAC ATT GGC GGG CTG TCT CCT AAG CAT GCC CCA GAT ATT CCT  257
Lys Gln Asp Ile Gly Gly Leu Ser Pro Lys His Ala Pro Asp Ile Pro
             45                  50                  55

GAT GAC AGC ACT GAC AAC ATC ACT ATC TTC ACC AGA ATC TTG GAT CGT  305
Asp Asp Ser Thr Asp Asn Ile Thr Ile Phe Thr Arg Ile Leu Asp Arg
             60                  65                  70

CTT CTG GAC GGC TAT GAC AAC CGG CTG CGA CCT GGG CTT GGA GAT GCA  353
Leu Leu Asp Gly Tyr Asp Asn Arg Leu Arg Pro Gly Leu Gly Asp Ala
             75                  80                  85

GTG ACT GAA GTG AAG ACT GAC ATC TAC GTG ACC AGT TTT GGC CCT GTG  401
Val Thr Glu Val Lys Thr Asp Ile Tyr Val Thr Ser Phe Gly Pro Val
 90              95                  100                 105

TCA GAC ACT GAC ATG GAG TAC ACT ATT GAT GTA TTT TTT CGG CAG ACA  449
Ser Asp Thr Asp Met Glu Tyr Thr Ile Asp Val Phe Phe Arg Gln Thr
                 110                 115                 120

TGG CAT GAT GAA AGA CTG AAA TTT GAT GGC CCC ATG AAG ATC CTT CCA  497
Trp His Asp Glu Arg Leu Lys Phe Asp Gly Pro Met Lys Ile Leu Pro
                 125                 130                 135

CTG AAC AAT CTC CTG GCT AGT AAG ATC TGG ACA CCG GAC ACC TTC TTC  545
Leu Asn Asn Leu Leu Ala Ser Lys Ile Trp Thr Pro Asp Thr Phe Phe
                 140                 145                 150
```

FIG.3A

```
CAC AAT GGC AAG AAA TCA GTG GCT CAT AAC ATG ACC ACG CCC AAC AAG    593
His Asn Gly Lys Lys Ser Val Ala His Asn Met Thr Thr Pro Asn Lys
        155             160             165

CTG CTC AGA TTG GTG GAC AAC GGA ACC CTC CTC TAT ACA ATG AGG TTA    641
Leu Leu Arg Leu Val Asp Asn Gly Thr Leu Leu Tyr Thr Met Arg Leu
170             175             180             185

ACA ATT CAT GCT GAG TGT CCC ATG CAT TTG GAA GAT TTT CCC ATG GAT    689
Thr Ile His Ala Glu Cys Pro Met His Leu Glu Asp Phe Pro Met Asp
            190             195             200

GTG CAT GCC TGC CCA CTG AAG TTT GGA AGC TAT GCC TAT ACA ACA GCT    737
Val His Ala Cys Pro Leu Lys Phe Gly Ser Tyr Ala Tyr Thr Thr Ala
            205             210             215

GAA GTG GTT TAT TCT TGG ACT CTC GGA AAG AAC AAA TCC GTG GAA GTG    785
Glu Val Val Tyr Ser Trp Thr Leu Gly Lys Asn Lys Ser Val Glu Val
            220             225             230

GCA CAG GAT GGT TCT CGC TTG AAC CAG TAT GAC CTT TTG GGC CAT GTT    833
Ala Gln Asp Gly Ser Arg Leu Asn Gln Tyr Asp Leu Leu Gly His Val
            235             240             245

GTT GGG ACA GAG ATA ATC CGG TCT AGT ACA GGA GAA TAT GTC GTC ATG    881
Val Gly Thr Glu Ile Ile Arg Ser Ser Thr Gly Glu Tyr Val Val Met
250             255             260             265

ACA ACC CAC TTC CAT CTC AAG CGA AAA ATT GGC TAC TTT GTG ATC CAG    929
Thr Thr His Phe His Leu Lys Arg Lys Ile Gly Tyr Phe Val Ile Gln
                270             275             280

ACC TAC TTG CCA TGT ATC ATG ACT GTC ATT CTG TCA CAA GTG TCG TTC    977
Thr Tyr Leu Pro Cys Ile Met Thr Val Ile Leu Ser Gln Val Ser Phe
            285             290             295

TGG CTC AAC AGA GAG TCT GTT CCT GCC CGT ACA GTC TTT GGT GTC ACC   1025
Trp Leu Asn Arg Glu Ser Val Pro Ala Arg Thr Val Phe Gly Val Thr
            300             305             310
```

FIG.3B

```
ACT GTG CTT ACC ATG ACC ACC TTG AGT ATC AGT GCC AGA AAT TCC TTA    1073
Thr Val Leu Thr Met Thr Thr Leu Ser Ile Ser Ala Arg Asn Ser Leu
    315             320                 325

CCT AAA GTG GCA TAT GCG ACG GCC ATG GAC TGG TTC ATA GCC GTC TGT    1121
Pro Lys Val Ala Tyr Ala Thr Ala Met Asp Trp Phe Ile Ala Val Cys
330             335                 340                 345

TAT GCC TTT GTA TTT TCT GCA CTG ATT GAA TTT GCC ACT GTC AAC TAT    1169
Tyr Ala Phe Val Phe Ser Ala Leu Ile Glu Phe Ala Thr Val Asn Tyr
                350                 355                 360

TTC ACC AAG CGG AGT TGG GCT TGG GAA GGC AAG AAG GTG CCA GAG GCC    1217
Phe Thr Lys Arg Ser Trp Ala Trp Glu Gly Lys Lys Val Pro Glu Ala
            365                 370                 375

CTG GAG ATG AAG AAG AAA ACA CCA GCA GCC CCA GCA AAG AAA ACC AGC    1265
Leu Glu Met Lys Lys Lys Thr Pro Ala Ala Pro Ala Lys Lys Thr Ser
            380                 385                 390

ACT ACC TTC AAC ATC GTG GGG ACC ACC TAT CCC ATC AAC CTG GCC AAG    1313
Thr Thr Phe Asn Ile Val Gly Thr Thr Tyr Pro Ile Asn Leu Ala Lys
            395                 400                 405

GAC ACT GAA TTT TCC ACC ATC TCC AAG GGC GCT GCT CCC AGT GCC TCC    1361
Asp Thr Glu Phe Ser Thr Ile Ser Lys Gly Ala Ala Pro Ser Ala Ser
410             415                 420                 425

TCA ACC CCA ACA ATC ATT GCT TCA CCC AAG GCC ACC TAC GTG CAG GAC    1409
Ser Thr Pro Thr Ile Ile Ala Ser Pro Lys Ala Thr Tyr Val Gln Asp
                430                 435                 440

AGC CCG ACT GAG ACC AAG ACC TAC AAC AGT GTC AGC AAG GTT GAC AAA    1457
Ser Pro Thr Glu Thr Lys Thr Tyr Asn Ser Val Ser Lys Val Asp Lys
                445                 450                 455

ATT TCC CGC ATC ATC TTT CCT GTG CTC TTT GCC ATA TTC AAT CTG GTC    1505
Ile Ser Arg Ile Ile Phe Pro Val Leu Phe Ala Ile Phe Asn Leu Val
            460                 465                 470
```

FIG.3C

```
TAT TGG GCC ACA TAT GTC AAC CGG GAG TCA GCT ATC AAG GGC ATG ATC    1553
Tyr Trp Ala Thr Tyr Val Asn Arg Glu Ser Ala Ile Lys Gly Met Ile
    475                 480                 485

CGC AAA CAG TAGATAGTGG CAGTGCAGCA ACCAGAGCAC TGTATACCCC            1602
Arg Lys Gln
490

GTGAAGCATC CAGGCACCCA AACCCCGGGG CTCCCC                            1638
```

FIG.3D

| | | |
|---|---|---|
| GAATTCCCCC CTTGCAGGCC GAGCCGGGGC CCTGCGCCCT CCCCCTCCGC CCAGCTCGGC | 60 |
| CAAGGGCGCA TTTGCTGAGC GTCTGGCGGC CTCTACCGGA GCACCTCTGC AGAGGGCCGA | 120 |
| TCCTCCAGCC CAGAGACGAC ATGTGGCGCT CGGGCGAGTG CCTTGCAGAG AGAGGAGTAG | 180 |
| CTTGCTGGCT TTGAACGCGT GGCGTGGCAG ATATTTCAGA AAGCTTCAAG AACAAGCTGG | 240 |
| AGAAGGGAAG AGTTATTCCT CCATATTCAC CTGCTTCAAC TACTATTCTT ATTGGGA | 297 |

```
ATG GAC AAT GGA ATG TTC TCT GGT TTT ATC ATG ATC AAA AAC CTC CTT    345
Met Asp Asn Gly Met Phe Ser Gly Phe Ile Met Ile Lys Asn Leu Leu
 1           5                  10                 15

CTC TTT TGT ATT TCC ATG AAC TTA TCC AGT CAC TTT GGC TTT TCA CAG    393
Leu Phe Cys Ile Ser Met Asn Leu Ser Ser His Phe Gly Phe Ser Gln
            20                  25                  30

ATG CCA ACC AGT TCA GTG AAA GAT GAG ACC AAT GAC AAC ATC ACG ATA    441
Met Pro Thr Ser Ser Val Lys Asp Glu Thr Asn Asp Asn Ile Thr Ile
        35                  40                  45

TTT ACC AGG ATC TTG GAT GGG CTC TTG GAT GGC TAC GAC AAC AGA CTT    489
Phe Thr Arg Ile Leu Asp Gly Leu Leu Asp Gly Tyr Asp Asn Arg Leu
    50                  55                  60

CGG CCC GGG CTG GGA GAG CGC ATC ACT CAG GTG AGG ACC GAC ATC TAC    537
Arg Pro Gly Leu Gly Glu Arg Ile Thr Gln Val Arg Thr Asp Ile Tyr
65                  70                  75                  80

GTC ACC AGC TTC GGC CCG GTG TCC GAC ACG GAA ATG GAG TAC ACC ATA    585
Val Thr Ser Phe Gly Pro Val Ser Asp Thr Glu Met Glu Tyr Thr Ile
                85                  90                  95

GAC GTG TTT TTC CGA CAA AGC TGG AAA GAT GAA AGG CTT CGG TTT AAG    633
Asp Val Phe Phe Arg Gln Ser Trp Lys Asp Glu Arg Leu Arg Phe Lys
            100                 105                 110

GGG CCC ATG CAG CGC CTC CCT CTC AAC AAC CTC CTT GCC AGC AAG ATC    681
Gly Pro Met Gln Arg Leu Pro Leu Asn Asn Leu Leu Ala Ser Lys Ile
        115                 120                 125
```

FIG.4A

| | |
|---|---|
| TGG ACC CCA GAC ACG TTC TTC CAC AAC GGG AAG AAG TCC ATC GCT CAC<br>Trp Thr Pro Asp Thr Phe Phe His Asn Gly Lys Lys Ser Ile Ala His<br>    130                          135                    140 | 729 |
| AAC ATG ACC ACG CCC AAC AAG CTG CTG CGG CTG GAG GAC GAC GGC ACC<br>Asn Met Thr Thr Pro Asn Lys Leu Leu Arg Leu Glu Asp Asp Gly Thr<br>145                    150                        155                        160 | 777 |
| CTG CTC TAC ACC ATG CGC TTG ACC ATC TCT GCA GAG TGC CCC ATG CAG<br>Leu Leu Tyr Thr Met Arg Leu Thr Ile Ser Ala Glu Cys Pro Met Gln<br>                    165                        170                        175 | 825 |
| CTT GAG GAC TTC CCG ATG GAT GCG CAC GCT TGC CCT CTG AAA TTT GGC<br>Leu Glu Asp Phe Pro Met Asp Ala His Ala Cys Pro Leu Lys Phe Gly<br>                180                        185                        190 | 873 |
| AGC TAT GCG TAC CCT AAT TCT GAA GTC GTT TAC GTC TGG ACC AAC GGC<br>Ser Tyr Ala Tyr Pro Asn Ser Glu Val Val Tyr Val Trp Thr Asn Gly<br>        195                        200                        205 | 921 |
| TCC ACC AAG TCG GTG GTG GTG GCG GAA GAT GGC TCC AGA CTG AAC CAG<br>Ser Thr Lys Ser Val Val Val Ala Glu Asp Gly Ser Arg Leu Asn Gln<br>210                                  215                        220 | 969 |
| TAC CAC CTG ATG GGG CAG ACG GTG GGC ACT GAG AAC ATC AGC ACC AGC<br>Tyr His Leu Met Gly Gln Thr Val Gly Thr Glu Asn Ile Ser Thr Ser<br>225                                  230                        235                        240 | 1017 |
| ACA GGC GAA TAC ACA ATC ATG ACA GCT CAC TTC CAC CTG AAA AGG AAG<br>Thr Gly Glu Tyr Thr Ile Met Thr Ala His Phe His Leu Lys Arg Lys<br>                        245                        250                        255 | 1065 |
| ATT GGC TAC TTT GTC ATC CAG ACC TAC CTT CCC TGC ATA ATG ACC GTG<br>Ile Gly Tyr Phe Val Ile Gln Thr Tyr Leu Pro Cys Ile Met Thr Val<br>                260                        265                        270 | 1113 |
| ATC TTA TCA CAG GTG TCC TTT TGG CTG AAC CGG GAA TCA GTC CCA GCC<br>Ile Leu Ser Gln Val Ser Phe Trp Leu Asn Arg Glu Ser Val Pro Ala<br>        275                        280                        285 | 1161 |
| AGG ACA GTT TTT GGG GTC ACC ACG GTG CTG ACC ATG ACG ACC CTC AGC<br>Arg Thr Val Phe Gly Val Thr Thr Val Leu Thr Met Thr Thr Leu Ser<br>290                                  295                        300 | 1209 |

FIG.4B

```
ATC AGC GCC AGG AAC TCT CTG CCC AAA GTG GCC TAC GCC ACC GCC ATG   1257
Ile Ser Ala Arg Asn Ser Leu Pro Lys Val Ala Tyr Ala Thr Ala Met
305                 310                315                320

GAC TGG TTC ATA GCT GTG TGC TAT GCC TTC GTC TTC TCG GCG CTG ATA   1305
Asp Trp Phe Ile Ala Val Cys Tyr Ala Phe Val Phe Ser Ala Leu Ile
                325                330                335

GAG TTT GCC ACG GTC AAT TAC TTT ACC AAG AGA GGC TGG GCC TGG GAT   1353
Glu Phe Ala Thr Val Asn Tyr Phe Thr Lys Arg Gly Trp Ala Trp Asp
                340                345                350

GGC AAA AAA GCC TTG GAA GCA GCC AAG ATC AAG AAA AAG CGT GAA GTC   1401
Gly Lys Lys Ala Leu Glu Ala Ala Lys Ile Lys Lys Lys Arg Glu Val
            355                360                365

ATA CTA AAT AAG TCA ACA AAC GCT TTT ACA ACT GGG AAG ATG TCT CAC   1449
Ile Leu Asn Lys Ser Thr Asn Ala Phe Thr Thr Gly Lys Met Ser His
    370                375                380

CCC CCA AAC ATT CCG AAG GAA CAG ACC CCA GCA GGG ACG TCG AAT ACA   1497
Pro Pro Asn Ile Pro Lys Glu Gln Thr Pro Ala Gly Thr Ser Asn Thr
385                390                395                400

ACC TCA GTC TCA GTA AAA CCC TCT GAA GAG AAG ACT TCT GAA AGC AAA   1545
Thr Ser Val Ser Val Lys Pro Ser Glu Glu Lys Thr Ser Glu Ser Lys
                405                410                415

AAG ACT TAC AAC AGT ATC AGC AAA ATT GAC AAA ATG TCC CGA ATC GTA   1593
Lys Thr Tyr Asn Ser Ile Ser Lys Ile Asp Lys Met Ser Arg Ile Val
                420                425                430

TTC CCA GTC TTG TTC GGC ACT TTC AAC TTA GTT TAC TGG GCA ACG TAT   1641
Phe Pro Val Leu Phe Gly Thr Phe Asn Leu Val Tyr Trp Ala Thr Tyr
            435                440                445

TTG AAT AGG GAG CCG GTG ATA AAA GGA GCC GCC TCT CCA AAA            1683
Leu Asn Arg Glu Pro Val Ile Lys Gly Ala Ala Ser Pro Lys
        450                455                460

TAACCGGCCA CACTCCCAAA CTCCAAGACA GCCATACTTC CAGCGAAATG GTACCAAGGA  1743

GAGGTTTTGC TCACAGGGAC TCTCCATATG TGAGCACTAT CTTTCAGGAA ATTTTTGCAT  1803
```

FIG.4C

```
GTTTAATAAT ATGTACAAAT AATATTGCCT TGATGTTTCT ATATGTAACT TCAGATGTTT 1863

CCAAGATGTC CCATTGATAA TTCGAGCAAA CAACTTTCTG GAAAAACAGG ATACGATGAC 1923

TGACACTCAG ATGCCCAGTA TCATACGTTG ATAGTTTACA AACAAGATAC GTATATTTTT 1983

AACTGCTTCA AGTGTTACCT AACAATGTTT TTTATACTTC AAATGTCATT TCATACAAAT 2043

TTTCCCAGTG AATAAATATT TTAGGAAACT CTCCATGATT ATTAGAAGAC CAACTATATT 2103

GCGAGAAACA GAGATCATAA AGAGCACGTT TTCCATTATG AGGAAACTTG GACATTTATG 2163

TACAAAATGA ATTGCCTTTG ATAATTCTTA CTGTTCTGAA ATTAGGAAAG TACTTGCATG 2223

ATCTTACACG AAGAAATAGA ATAGGCAAAC TTTTATGTAG GCAGATTAAT AACAGAAATA 2283

CATCATATGT TAGATACACA AAATATT                                     2310
```

FIG.4D

```
AATTCTGCAT TTCAGTGCAC TGCAGG ATG GCG TCA TCT CTG CCC TGG CTG TGC    53
                            Met Ala Ser Ser Leu Pro Trp Leu Cys
                             1               5

ATT ATT CTG TGG CTA GAA AAT GCC CTA GGG AAA CTC GAA GTT GAA GGC  101
           Ile Ile Leu Trp Leu Glu Asn Ala Leu Gly Lys Leu Glu Val Glu Gly
            10              15              20              25

AAC TTC TAC TCA GAA AAC GTC AGT CGG ATC CTG GAC AAC TTG CTT GAA  149
           Asn Phe Tyr Ser Glu Asn Val Ser Arg Ile Leu Asp Asn Leu Leu Glu
                           30              35              40

GGC TAT GAC AAT CGG CTG CGG CCG GGA TTT GGA GGT GCT GTC ACT GAA  197
           Gly Tyr Asp Asn Arg Leu Arg Pro Gly Phe Gly Gly Ala Val Thr Glu
                           45              50              55

GTC AAA ACA GAC ATT TAT GTG ACC AGT TTT GGG CCC GTG TCA GAT GTG  245
           Val Lys Thr Asp Ile Tyr Val Thr Ser Phe Gly Pro Val Ser Asp Val
                           60              65              70

GAG ATG GAG TAT ACG ATG GAT GTT TTT TTT CGC CAG ACC TGG ACT GAT  293
           Glu Met Glu Tyr Thr Met Asp Val Phe Phe Arg Gln Thr Trp Thr Asp
            75              80              85

GAG AGG TTG AAG TTT GGG GGG CCA ACT GAG ATT CTG AGT CTG AAT AAT  341
           Glu Arg Leu Lys Phe Gly Gly Pro Thr Glu Ile Leu Ser Leu Asn Asn
            90              95             100             105

TTG ATG GTC AGT AAA ATC TGG ACG CCT GAC ACC TTT TTC AGA AAT GGT  389
           Leu Met Val Ser Lys Ile Trp Thr Pro Asp Thr Phe Phe Arg Asn Gly
                          110             115             120

AAA AAG TCC ATT GCT CAC AAC ATG ACA ACT CCT AAT AAA CTC TTC AGA  437
           Lys Lys Ser Ile Ala His Asn Met Thr Thr Pro Asn Lys Leu Phe Arg
                          125             130             135

ATA ATG CAG AAT GGA ACC ATT TTA TAC ACC ATG AGG CTT ACC ATC AAT  485
           Ile Met Gln Asn Gly Thr Ile Leu Tyr Thr Met Arg Leu Thr Ile Asn
                          140             145             150

GCT GAC TGT CCC ATG AGG CTG GTT AAC TTT CCT ATG GAT GGG CAT GCT  533
           Ala Asp Cys Pro Met Arg Leu Val Asn Phe Pro Met Asp Gly His Ala
                          155             160             165
```

FIG.5A

```
TGT CCA CTC AAG TTT GGG AGC TAT GCT TAT CCC AAA AGT GAA ATC ATA    581
Cys Pro Leu Lys Phe Gly Ser Tyr Ala Tyr Pro Lys Ser Glu Ile Ile
170             175             180             185

TAT ACG TGG AAA AAA GGA CCA CTT TAC TCA GTA GAA GTC CCA GAA GAA    629
Tyr Thr Trp Lys Lys Gly Pro Leu Tyr Ser Val Glu Val Pro Glu Glu
                190             195             200

TCT TCA AGC CTT CTC CAG TAT GAT CTG ATT GGA CAA ACA GTA TCT AGT    677
Ser Ser Ser Leu Leu Gln Tyr Asp Leu Ile Gly Gln Thr Val Ser Ser
            205             210             215

GAG ACA ATT AAA TCT AAC ACA GGT GAA TAC GTT ATA ATG ACA GTT TAC    725
Glu Thr Ile Lys Ser Asn Thr Gly Glu Tyr Val Ile Met Thr Val Tyr
        220             225             230

TTC CAC TTG CAA AGG AAG ATG GGC TAC TTC ATG ATA CAG ATA TAC ACT    773
Phe His Leu Gln Arg Lys Met Gly Tyr Phe Met Ile Gln Ile Tyr Thr
    235             240             245

CCT TGC ATT ATG ACA GTC ATT CTT TCC CAG GTG TCT TTC TGG ATT AAT    821
Pro Cys Ile Met Thr Val Ile Leu Ser Gln Val Ser Phe Trp Ile Asn
250             255             260             265

AAG GAG TCC GTC CCA GCA AGA ACT GTT CTT GGG ATC ACC ACT GTT TTA    869
Lys Glu Ser Val Pro Ala Arg Thr Val Leu Gly Ile Thr Thr Val Leu
                270             275             280

ACT ATG ACC ACT TTG AGC ATC AGT GCC CGG CAC TCT TTG CCA AAA GTG    917
Thr Met Thr Thr Leu Ser Ile Ser Ala Arg His Ser Leu Pro Lys Val
            285             290             295

TCA TAT GCC ACT GCC ATG GAT TGG TTC ATA GCT GTT TGC TTT GCA TTC    965
Ser Tyr Ala Thr Ala Met Asp Trp Phe Ile Ala Val Cys Phe Ala Phe
        300             305             310

GTC TTC TCT GCT CTT ATC GAG TTC GCA GCT GTC AAC TAC TTT ACC AAT   1013
Val Phe Ser Ala Leu Ile Glu Phe Ala Ala Val Asn Tyr Phe Thr Asn
    315             320             325
```

FIG.5B

```
CTT CAG ACA CAG AAG GCG AAA AGG AAG GCA CAG TTT GCA GCC CCA CCC   1061
Leu Gln Thr Gln Lys Ala Lys Arg Lys Ala Gln Phe Ala Ala Pro Pro
330             335             340             345

ACA GTG ACA ATA TCA AAA GCT ACT GAA CCT TTG GAA GCT GAG ATT GTT   1109
Thr Val Thr Ile Ser Lys Ala Thr Glu Pro Leu Glu Ala Glu Ile Val
                350             355             360

TTG CAT CCT GAC TCC AAA TAT CAT CTG AAG AAA AGG ATC ACT TCT CTG   1157
Leu His Pro Asp Ser Lys Tyr His Leu Lys Lys Arg Ile Thr Ser Leu
            365             370             375

TCT TTG CCA ATA GTT TCA TCT TCC GAG GCC AAT AAA GTG CTC ACG AGA   1205
Ser Leu Pro Ile Val Ser Ser Ser Glu Ala Asn Lys Val Leu Thr Arg
        380             385             390

GCG CCC ATC TTA CAA TCA ACA CCT GTC ACA CCC CCA CCA CTC CCG CCA   1253
Ala Pro Ile Leu Gln Ser Thr Pro Val Thr Pro Pro Pro Leu Pro Pro
    395             400             405

GCC TTT GGA GGC ACC AGT AAA ATA GAC CAG TAT TCT CGA ATT CTC TTC   1301
Ala Phe Gly Gly Thr Ser Lys Ile Asp Gln Tyr Ser Arg Ile Leu Phe
410             415             420             425

CCA GTT GCA TTT GCA GGA TTC AAC CTT GTG TAC TGG GTA GTT TAT CTT   1349
Pro Val Ala Phe Ala Gly Phe Asn Leu Val Tyr Trp Val Val Tyr Leu
                430             435             440

TCC AAA GAT ACA ATG GAA GTG AGT AGC AGT GTT GAA TAGCTTTTCC        1395
Ser Lys Asp Thr Met Glu Val Ser Ser Ser Val Glu
            445             450

AGGACAACCT GAA                                                    1408
```

FIG.5C

```
GAATTCCGCG CGGGGAAGGG AAGAAGAGGA CGAGGTGGCG CAGAGACCGC GGGAGAACAC   60

AGTGCCTCCG GAGGAAATCT GCTCGGTCCC CGGCAGCCGC GCTTCCCCTT TGATGTTTTG  120

GTACGCCGTG GCCATGCGCC TCACATTAGA ATTACTGCAC TGGGCAGACT AAGTTGGATC  180

TCCTCTCTTC AGTGAAACCC TCAATTCCAT CAAAAACTAA AGGG ATG TGG AGA GTG  236
                                              Met Trp Arg Val
                                               1
```

| | | | | | | | | | | | | | | | | |
|---|---|---|---|---|---|---|---|---|---|---|---|---|---|---|---|---|
| CGG | AAA | AGG | GGC | TAC | TTT | GGG | ATT | TGG | TCC | TTC | CCC | TTA | ATA | ATC | GCC | 284 |
| Arg | Lys | Arg | Gly | Tyr | Phe | Gly | Ile | Trp | Ser | Phe | Pro | Leu | Ile | Ile | Ala | |
| | 5 | | | 10 | | | | 15 | | | | | | 20 | | |
| GCT | GTC | TGT | GCG | CAG | AGT | GTC | AAT | GAC | CCT | AGT | AAT | ATG | TCG | CTG | GTT | 332 |
| Ala | Val | Cys | Ala | Gln | Ser | Val | Asn | Asp | Pro | Ser | Asn | Met | Ser | Leu | Val | |
| | | | | 25 | | | | | 30 | | | | | 35 | | |
| AAA | GAG | ACG | GTG | GAT | AGA | CTC | CTG | AAA | GGC | TAT | GAC | ATT | CGT | CTG | AGA | 380 |
| Lys | Glu | Thr | Val | Asp | Arg | Leu | Leu | Lys | Gly | Tyr | Asp | Ile | Arg | Leu | Arg | |
| | | | 40 | | | | | 45 | | | | | 50 | | | |
| CCA | GAT | TTT | GGA | GGT | CCC | CCC | GTG | GCT | GTG | GGG | ATG | AAC | ATT | GAC | ATT | 428 |
| Pro | Asp | Phe | Gly | Gly | Pro | Pro | Val | Ala | Val | Gly | Met | Asn | Ile | Asp | Ile | |
| | | | 55 | | | | 60 | | | | | 65 | | | | |
| GCC | AGC | ATC | GAT | ATG | GTT | TCT | GAA | GTC | AAT | ATG | GAT | TAT | ACC | TTG | ACA | 476 |
| Ala | Ser | Ile | Asp | Met | Val | Ser | Glu | Val | Asn | Met | Asp | Tyr | Thr | Leu | Thr | |
| | | 70 | | | | 75 | | | | | 80 | | | | | |
| ATG | TAC | TTT | CAA | CAA | GCC | TGG | AGA | GAT | AAG | AGG | CTG | TCC | TAT | AAT | GTA | 524 |
| Met | Tyr | Phe | Gln | Gln | Ala | Trp | Arg | Asp | Lys | Arg | Leu | Ser | Tyr | Asn | Val | |
| | 85 | | | | 90 | | | | 95 | | | | | 100 | | |
| ATA | CCT | TTA | AAC | TTG | ACT | CTG | GAC | AAC | AGA | GTG | GCA | GAC | CAG | CTC | TGG | 572 |
| Ile | Pro | Leu | Asn | Leu | Thr | Leu | Asp | Asn | Arg | Val | Ala | Asp | Gln | Leu | Trp | |
| | | | | 105 | | | | | 110 | | | | | 115 | | |
| GTG | CCT | GAT | ACC | TAT | TTC | CTG | AAC | GAT | AAG | AAG | TCA | TTT | GTG | CAC | GGA | 620 |
| Val | Pro | Asp | Thr | Tyr | Phe | Leu | Asn | Asp | Lys | Lys | Ser | Phe | Val | His | Gly | |
| | | | 120 | | | | | 125 | | | | | 130 | | | |

FIG.6A

```
GTG ACT GTT AAG AAC CGC ATG ATT CGC CTG CAT CCT GAT GGC ACC GTC    668
Val Thr Val Lys Asn Arg Met Ile Arg Leu His Pro Asp Gly Thr Val
        135                 140                 145

CTT TAT GGA CTC AGA ATC ACA ACC ACA GCT GCC TGC ATG ATG GAC CTA    716
Leu Tyr Gly Leu Arg Ile Thr Thr Thr Ala Ala Cys Met Met Asp Leu
    150                 155                 160

AGG AGG TAC CCA CTG GAT GAA CAA AAC TGC ACC TTG GAA ATT GAG AGC    764
Arg Arg Tyr Pro Leu Asp Glu Gln Asn Cys Thr Leu Glu Ile Glu Ser
165                 170                 175                 180

TAT GGA TAC ACA ACT GAT GAC ATT GAG TTT TAC TGG CGT GGC GAT GAT    812
Tyr Gly Tyr Thr Thr Asp Asp Ile Glu Phe Tyr Trp Arg Gly Asp Asp
                185                 190                 195

AAT GCA GTA ACA GGA GTA ACG AAA ATT GAA CTT CCA CAG TTC TCT ATT    860
Asn Ala Val Thr Gly Val Thr Lys Ile Glu Leu Pro Gln Phe Ser Ile
            200                 205                 210

GTA GAT TAC AAA CTT ATC ACC AAG AAG GTT GTT TTT TCC ACA GGT TCC    908
Val Asp Tyr Lys Leu Ile Thr Lys Lys Val Val Phe Ser Thr Gly Ser
        215                 220                 225

TAT CCC AGG TTA TCC CTC AGC TTT AAG CTT AAG AGA AAC ATT GGC TAC    956
Tyr Pro Arg Leu Ser Leu Ser Phe Lys Leu Lys Arg Asn Ile Gly Tyr
    230                 235                 240

TTT ATC CTG CAA ACA TAC ATG CCT TCC ATC CTG ATT ACC ATC CTC TCC   1004
Phe Ile Leu Gln Thr Tyr Met Pro Ser Ile Leu Ile Thr Ile Leu Ser
245                 250                 255                 260

TGG GTC TCC TTC TGG ATT AAT TAC GAT GCT TCA GCT GCA AGG GTG GCA   1052
Trp Val Ser Phe Trp Ile Asn Tyr Asp Ala Ser Ala Ala Arg Val Ala
                265                 270                 275

TTA GGA ATC ACA ACT GTC CTC ACA ATG ACC ACA ATC AAC ACC CAC CTC   1100
Leu Gly Ile Thr Thr Val Leu Thr Met Thr Thr Ile Asn Thr His Leu
            280                 285                 290

CGG GAA ACT CTC CCT AAA ATC CCC TAT GTG AAG GCC ATT GAC ATG TAC   1148
Arg Glu Thr Leu Pro Lys Ile Pro Tyr Val Lys Ala Ile Asp Met Tyr
        295                 300                 305
```

FIG.6B

```
CTG ATG GGG TGC TTT GTC TTC GTT TTC ATG GCC CTT CTG GAA TAT GCC    1196
Leu Met Gly Cys Phe Val Phe Val Phe Met Ala Leu Leu Glu Tyr Ala
        310                 315                 320

CTA GTC AAC TAC ATC TTC TTT GGG AGG GGG CCC CAA CGC CAA AAG AAA    1244
Leu Val Asn Tyr Ile Phe Phe Gly Arg Gly Pro Gln Arg Gln Lys Lys
325                 330                 335                 340

GCA GCT GAG AAG GCT GCC AGT GCC AAC AAT GAG AAG ATG CGC CTG GAT    1292
Ala Ala Glu Lys Ala Ala Ser Ala Asn Asn Glu Lys Met Arg Leu Asp
                345                 350                 355

GTC AAC AAG ATG GAC CCC CAT GAG AAC ATC TTA CTG AGC ACT CTC GAG    1340
Val Asn Lys Met Asp Pro His Glu Asn Ile Leu Leu Ser Thr Leu Glu
            360                 365                 370

ATA AAA AAT GAA ATG GCC ACA TCT GAG GCT GTG ATG GGA CTT GGA GAC    1388
Ile Lys Asn Glu Met Ala Thr Ser Glu Ala Val Met Gly Leu Gly Asp
        375                 380                 385

CCC AGA AGC ACA ATG CTA GCC TAT GAT GCC TCC AGC ATC CAG TAT CGG    1436
Pro Arg Ser Thr Met Leu Ala Tyr Asp Ala Ser Ser Ile Gln Tyr Arg
    390                 395                 400

AAA GCT GGG TTG CCC AGG CAT AGT TTT GGC CGA AAT GCT CTG GAA CGA    1484
Lys Ala Gly Leu Pro Arg His Ser Phe Gly Arg Asn Ala Leu Glu Arg
405                 410                 415                 420

CAT GTG GCG CAA AAG AAA AGT CGC CTG AGG AGA CGC GCC TCC CAA CTG    1532
His Val Ala Gln Lys Lys Ser Arg Leu Arg Arg Arg Ala Ser Gln Leu
                425                 430                 435

AAA ATC ACC ATC CCT GAC TTG ACT GAT GTG AAT GCC ATA GAT CGG TGG    1580
Lys Ile Thr Ile Pro Asp Leu Thr Asp Val Asn Ala Ile Asp Arg Trp
            440                 445                 450

TCC CGC ATA TTC TTC CCA GTG GTT TTT TCC TTC TTC AAC ATC GTC TAT    1628
Ser Arg Ile Phe Phe Pro Val Val Phe Ser Phe Phe Asn Ile Val Tyr
        455                 460                 465

TGG CTT TAT TAT GTG AAC TAAAACATGG CCTCCCACTG GAAGCAAGGA           1676
Trp Leu Tyr Tyr Val Asn
    470
```

FIG.6C

```
CTAGATTCCT CCTCAAACCA GTTGTACAGC CTGATGTAGG ACTTGGAAAA CACATCAATC 1736

CAGGACAAAA GTGACGCTAA AATACCTTAG TTGCTGGCCT ATCCTGTGGT CCATTTCATA 1796

CCATTTGGGT TGCTTCTGCT AAGTAATGAA TACACTAAGG TCCTTGTGGT TTTCCAGTTA 1856

AAACGCAAGT                                                      1866
```

FIG.6D

SEQUENCE LISTING ( 1 ) GENERAL INFORMATION:

( i i i ) NUMBER OF SEQUENCES: 25

( 2 ) INFORMATION FOR SEQ ID NO: 1:

( i ) SEQUENCE CHARACTERISTICS:
        ( A ) LENGTH: 2310 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 298..1683

( x i ) SEQUENCE DESCRIPTION: SEQ ID NO: 1:

```
GAATTCCCCC  CTTGCAGGCC  GAGCCGGGGC  CCTGCGCCCT  CCCCCTCCGC  CCAGCTCGGC    60

CAAGGGCGCA  TTTGCTGAGC  GTCTGGCGGC  CTCTACCGGA  GCACCTCTGC  AGAGGGCCGA   120

TCCTCCAGCC  CAGAGACGAC  ATGTGGCGCT  CGGGCGAGTG  CCTTGCAGAG  AGAGGAGTAG   180

CTTGCTGGCT  TTGAACGCGT  GGCGTGGCAG  ATATTTCAGA  AAGCTTCAAG  AACAAGCTGG   240

AGAAGGGAAG  AGTTATTCCT  CCATATTCAC  CTGCTTCAAC  TACTATTCTT  ATTGGGA     297
```

| | | | | | | | | | | | | | | | | |
|---|---|---|---|---|---|---|---|---|---|---|---|---|---|---|---|---|
| ATG | GAC | AAT | GGA | ATG | TTC | TCT | GGT | TTT | ATC | ATG | ATC | AAA | AAC | CTC | CTT | 345 |
| Met | Asp | Asn | Gly | Met | Phe | Ser | Gly | Phe | Ile | Met | Ile | Lys | Asn | Leu | Leu | |
| 1 | | | | 5 | | | | | 10 | | | | | 15 | | |
| CTC | TTT | TGT | ATT | TCC | ATG | AAC | TTA | TCC | AGT | CAC | TTT | GGC | TTT | TCA | CAG | 393 |
| Leu | Phe | Cys | Ile | Ser | Met | Asn | Leu | Ser | Ser | His | Phe | Gly | Phe | Ser | Gln | |
| | | | 20 | | | | | 25 | | | | | 30 | | | |
| ATG | CCA | ACC | AGT | TCA | GTG | AAA | GAT | GAG | ACC | AAT | GAC | AAC | ATC | ACG | ATA | 441 |
| Met | Pro | Thr | Ser | Ser | Val | Lys | Asp | Glu | Thr | Asn | Asp | Asn | Ile | Thr | Ile | |
| | | 35 | | | | | 40 | | | | | 45 | | | | |
| TTT | ACC | AGG | ATC | TTG | GAT | GGG | CTC | TTG | GAT | GGC | TAC | GAC | AAC | AGA | CTT | 489 |
| Phe | Thr | Arg | Ile | Leu | Asp | Gly | Leu | Leu | Asp | Gly | Tyr | Asp | Asn | Arg | Leu | |
| | 50 | | | | | 55 | | | | | 60 | | | | | |
| CGG | CCC | GGG | CTG | GGA | GAG | CGC | ATC | ACT | CAG | GTG | AGG | ACC | GAC | ATC | TAC | 537 |
| Arg | Pro | Gly | Leu | Gly | Glu | Arg | Ile | Thr | Gln | Val | Arg | Thr | Asp | Ile | Tyr | |
| 65 | | | | | 70 | | | | | 75 | | | | | 80 | |
| GTC | ACC | AGC | TTC | GGC | CCG | GTG | TCC | GAC | ACG | GAA | ATG | GAG | TAC | ACC | ATA | 585 |
| Val | Thr | Ser | Phe | Gly | Pro | Val | Ser | Asp | Thr | Glu | Met | Glu | Tyr | Thr | Ile | |
| | | | | 85 | | | | | 90 | | | | | 95 | | |
| GAC | GTG | TTT | TTC | CGA | CAA | AGC | TGG | AAA | GAT | GAA | AGG | CTT | CGG | TTT | AAG | 633 |
| Asp | Val | Phe | Phe | Arg | Gln | Ser | Trp | Lys | Asp | Glu | Arg | Leu | Arg | Phe | Lys | |
| | | | 100 | | | | | 105 | | | | | 110 | | | |
| GGG | CCC | ATG | CAG | CGC | CTC | CCT | CTC | AAC | AAC | CTC | CTT | GCC | AGC | AAG | ATC | 681 |
| Gly | Pro | Met | Gln | Arg | Leu | Pro | Leu | Asn | Asn | Leu | Leu | Ala | Ser | Lys | Ile | |
| | | 115 | | | | | 120 | | | | | 125 | | | | |
| TGG | ACC | CCA | GAC | ACG | TTC | TTC | CAC | AAC | GGG | AAG | AAG | TCC | ATC | GCT | CAC | 729 |
| Trp | Thr | Pro | Asp | Thr | Phe | Phe | His | Asn | Gly | Lys | Lys | Ser | Ile | Ala | His | |
| | 130 | | | | | 135 | | | | | 140 | | | | | |
| AAC | ATG | ACC | ACG | CCC | AAC | AAG | CTG | CTG | CGG | CTG | GAG | GAC | GAC | GGC | ACC | 777 |
| Asn | Met | Thr | Thr | Pro | Asn | Lys | Leu | Leu | Arg | Leu | Glu | Asp | Asp | Gly | Thr | |
| 145 | | | | | 150 | | | | | 155 | | | | | 160 | |
| CTG | CTC | TAC | ACC | ATG | CGC | TTG | ACC | ATC | TCT | GCA | GAG | TGC | CCC | ATG | CAG | 825 |
| Leu | Leu | Tyr | Thr | Met | Arg | Leu | Thr | Ile | Ser | Ala | Glu | Cys | Pro | Met | Gln | |
| | | | | 165 | | | | | 170 | | | | | 175 | | |
| CTT | GAG | GAC | TTC | CCG | ATG | GAT | GCG | CAC | GCT | TGC | CCT | CTG | AAA | TTT | GGC | 873 |
| Leu | Glu | Asp | Phe | Pro | Met | Asp | Ala | His | Ala | Cys | Pro | Leu | Lys | Phe | Gly | |
| | | | 180 | | | | | 185 | | | | | 190 | | | |
| AGC | TAT | GCG | TAC | CCT | AAT | TCT | GAA | GTC | GTT | TAC | GTC | TGG | ACC | AAC | GGC | 921 |
| Ser | Tyr | Ala | Tyr | Pro | Asn | Ser | Glu | Val | Val | Tyr | Val | Trp | Thr | Asn | Gly | |
| | | 195 | | | | | 200 | | | | | 205 | | | | |
| TCC | ACC | AAG | TCG | GTG | GTG | GTG | GCG | GAA | GAT | GGC | TCC | AGA | CTG | AAC | CAG | 969 |
| Ser | Thr | Lys | Ser | Val | Val | Val | Ala | Glu | Asp | Gly | Ser | Arg | Leu | Asn | Gln | |
| | 210 | | | | | 215 | | | | | 220 | | | | | |
| TAC | CAC | CTG | ATG | GGG | CAG | ACG | GTG | GGC | ACT | GAG | AAC | ATC | AGC | ACC | AGC | 1017 |
| Tyr | His | Leu | Met | Gly | Gln | Thr | Val | Gly | Thr | Glu | Asn | Ile | Ser | Thr | Ser | |
| 225 | | | | | 230 | | | | | 235 | | | | | 240 | |
| ACA | GGC | GAA | TAC | ACA | ATC | ATG | ACA | GCT | CAC | TTC | CAC | CTG | AAA | AGG | AAG | 1065 |
| Thr | Gly | Glu | Tyr | Thr | Ile | Met | Thr | Ala | His | Phe | His | Leu | Lys | Arg | Lys | |
| | | | | 245 | | | | | 250 | | | | | 255 | | |
| ATT | GGC | TAC | TTT | GTC | ATC | CAG | ACC | TAC | CTT | CCC | TGC | ATA | ATG | ACC | GTG | 1113 |
| Ile | Gly | Tyr | Phe | Val | Ile | Gln | Thr | Tyr | Leu | Pro | Cys | Ile | Met | Thr | Val | |
| | | | 260 | | | | | 265 | | | | | 270 | | | |
| ATC | TTA | TCA | CAG | GTG | TCC | TTT | TGG | CTG | AAC | CGG | GAA | TCA | GTC | CCA | GCC | 1161 |
| Ile | Leu | Ser | Gln | Val | Ser | Phe | Trp | Leu | Asn | Arg | Glu | Ser | Val | Pro | Ala | |
| | | 275 | | | | | 280 | | | | | 285 | | | | |
| AGG | ACA | GTT | TTT | GGG | GTC | ACC | ACG | GTG | CTG | ACC | ATG | ACG | ACC | CTC | AGC | 1209 |
| Arg | Thr | Val | Phe | Gly | Val | Thr | Thr | Val | Leu | Thr | Met | Thr | Thr | Leu | Ser | |
| | 290 | | | | | 295 | | | | | 300 | | | | | |
| ATC | AGC | GCC | AGG | AAC | TCT | CTG | CCC | AAA | GTG | GCC | TAC | GCC | ACC | GCC | ATG | 1257 |
| Ile | Ser | Ala | Arg | Asn | Ser | Leu | Pro | Lys | Val | Ala | Tyr | Ala | Thr | Ala | Met | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| GAC | TGG | TTC | ATA | GCT | GTG | TGC | TAT | GCC | TTC | GTC | TTC | TCG | GCG | CTG | ATA | 1305 |
| Asp | Trp | Phe | Ile | Ala | Val | Cys | Tyr | Ala | Phe | Val | Phe | Ser | Ala | Leu | Ile | |
| | | | 325 | | | | | 330 | | | | | | 335 | | |
| GAG | TTT | GCC | ACG | GTC | AAT | TAC | TTT | ACC | AAG | AGA | GGC | TGG | GCC | TGG | GAT | 1353 |
| Glu | Phe | Ala | Thr | Val | Asn | Tyr | Phe | Thr | Lys | Arg | Gly | Trp | Ala | Trp | Asp | |
| | | | 340 | | | | | 345 | | | | | 350 | | | |
| GGC | AAA | AAA | GCC | TTG | GAA | GCA | GCC | AAG | ATC | AAG | AAA | AAG | CGT | GAA | GTC | 1401 |
| Gly | Lys | Lys | Ala | Leu | Glu | Ala | Ala | Lys | Ile | Lys | Lys | Lys | Arg | Glu | Val | |
| | | 355 | | | | | 360 | | | | | 365 | | | | |
| ATA | CTA | AAT | AAG | TCA | ACA | AAC | GCT | TTT | ACA | ACT | GGG | AAG | ATG | TCT | CAC | 1449 |
| Ile | Leu | Asn | Lys | Ser | Thr | Asn | Ala | Phe | Thr | Thr | Gly | Lys | Met | Ser | His | |
| | | 370 | | | | | 375 | | | | | 380 | | | | |
| CCC | CCA | AAC | ATT | CCG | AAG | GAA | CAG | ACC | CCA | GCA | GGG | ACG | TCG | AAT | ACA | 1497 |
| Pro | Pro | Asn | Ile | Pro | Lys | Glu | Gln | Thr | Pro | Ala | Gly | Thr | Ser | Asn | Thr | |
| 385 | | | | | 390 | | | | | 395 | | | | | 400 | |
| ACC | TCA | GTC | TCA | GTA | AAA | CCC | TCT | GAA | GAG | AAG | ACT | TCT | GAA | AGC | AAA | 1545 |
| Thr | Ser | Val | Ser | Val | Lys | Pro | Ser | Glu | Glu | Lys | Thr | Ser | Glu | Ser | Lys | |
| | | | | 405 | | | | | 410 | | | | | 415 | | |
| AAG | ACT | TAC | AAC | AGT | ATC | AGC | AAA | ATT | GAC | AAA | ATG | TCC | CGA | ATC | GTA | 1593 |
| Lys | Thr | Tyr | Asn | Ser | Ile | Ser | Lys | Ile | Asp | Lys | Met | Ser | Arg | Ile | Val | |
| | | | 420 | | | | | 425 | | | | | 430 | | | |
| TTC | CCA | GTC | TTG | TTC | GGC | ACT | TTC | AAC | TTA | GTT | TAC | TGG | GCA | ACG | TAT | 1641 |
| Phe | Pro | Val | Leu | Phe | Gly | Thr | Phe | Asn | Leu | Val | Tyr | Trp | Ala | Thr | Tyr | |
| | | 435 | | | | | 440 | | | | | 445 | | | | |
| TTG | AAT | AGG | GAG | CCG | GTG | ATA | AAA | GGA | GCC | GCC | TCT | CCA | AAA | | | 1683 |
| Leu | Asn | Arg | Glu | Pro | Val | Ile | Lys | Gly | Ala | Ala | Ser | Pro | Lys | | | |
| | 450 | | | | | 455 | | | | | 460 | | | | | |

| | | | | |
|---|---|---|---|---|
| TAACCGGCCA | CACTCCCAAA | CTCCAAGACA | GCCATACTTC | CAGCGAAATG | GTACCAAGGA | 1743 |
| GAGGTTTTGC | TCACAGGGAC | TCTCCATATG | TGAGCACTAT | CTTTCAGGAA | ATTTTTGCAT | 1803 |
| GTTTAATAAT | ATGTACAAAT | AATATTGCCT | TGATGTTTCT | ATATGTAACT | TCAGATGTTT | 1863 |
| CCAAGATGTC | CCATTGATAA | TTCGAGCAAA | CAACTTTCTG | GAAAACAGG | ATACGATGAC | 1923 |
| TGACACTCAG | ATGCCCAGTA | TCATACGTTG | ATAGTTTACA | AACAAGATAC | GTATATTTT | 1983 |
| AACTGCTTCA | AGTGTTACCT | AACAATGTTT | TTTATACTTC | AAATGTCATT | TCATACAAAT | 2043 |
| TTTCCAGTG | AATAAATATT | TTAGGAAACT | CTCCATGATT | ATTAGAAGAC | CAACTATATT | 2103 |
| GCGAGAAACA | GAGATCATAA | AGAGCACGTT | TTCCATTATG | AGGAAACTTG | GACATTTATG | 2163 |
| TACAAAATGA | ATTGCCTTTG | ATAATTCTTA | CTGTTCTGAA | ATTAGGAAAG | TACTTGCATG | 2223 |
| ATCTTACACG | AAGAAATAGA | ATAGGCAAAC | TTTTATGTAG | GCAGATTAAT | AACAGAAATA | 2283 |
| CATCATATGT | TAGATACACA | AAATATT | | | | 2310 |

( 2 ) INFORMATION FOR SEQ ID NO: 2:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | |
|---|---|---|---|---|---|---|---|---|---|---|---|---|---|---|
| Met | Asp | Asn | Gly | Met | Phe | Ser | Gly | Phe | Ile | Met | Ile | Lys | Asn | Leu | Leu |
| 1 | | | | 5 | | | | | 10 | | | | | 15 | |
| Leu | Phe | Cys | Ile | Ser | Met | Asn | Leu | Ser | Ser | His | Phe | Gly | Phe | Ser | Gln |
| | | | 20 | | | | | 25 | | | | | 30 | | |
| Met | Pro | Thr | Ser | Ser | Val | Lys | Asp | Glu | Thr | Asn | Asp | Asn | Ile | Thr | Ile |
| | | | 35 | | | | | 40 | | | | | 45 | | |

```
Phe  Thr  Arg  Ile  Leu  Asp  Gly  Leu  Leu  Asp  Gly  Tyr  Asp  Asn  Arg  Leu
     50                  55                  60

Arg  Pro  Gly  Leu  Gly  Glu  Arg  Ile  Thr  Gln  Val  Arg  Thr  Asp  Ile  Tyr
65                       70                  75                           80

Val  Thr  Ser  Phe  Gly  Pro  Val  Ser  Asp  Thr  Glu  Met  Glu  Tyr  Thr  Ile
               85                       90                            95

Asp  Val  Phe  Phe  Arg  Gln  Ser  Trp  Lys  Asp  Glu  Arg  Leu  Arg  Phe  Lys
               100                      105                      110

Gly  Pro  Met  Gln  Arg  Leu  Pro  Leu  Asn  Asn  Leu  Leu  Ala  Ser  Lys  Ile
          115                      120                      125

Trp  Thr  Pro  Asp  Thr  Phe  Phe  His  Asn  Gly  Lys  Lys  Ser  Ile  Ala  His
     130                      135                      140

Asn  Met  Thr  Thr  Pro  Asn  Lys  Leu  Leu  Arg  Leu  Glu  Asp  Asp  Gly  Thr
145                      150                      155                      160

Leu  Leu  Tyr  Thr  Met  Arg  Leu  Thr  Ile  Ser  Ala  Glu  Cys  Pro  Met  Gln
               165                      170                      175

Leu  Glu  Asp  Phe  Pro  Met  Asp  Ala  His  Ala  Cys  Pro  Leu  Lys  Phe  Gly
               180                      185                      190

Ser  Tyr  Ala  Tyr  Pro  Asn  Ser  Glu  Val  Val  Tyr  Val  Trp  Thr  Asn  Gly
          195                      200                      205

Ser  Thr  Lys  Ser  Val  Val  Ala  Glu  Asp  Gly  Ser  Arg  Leu  Asn  Gln
     210                      215                      220

Tyr  His  Leu  Met  Gly  Gln  Thr  Val  Gly  Thr  Glu  Asn  Ile  Ser  Thr  Ser
225                      230                      235                      240

Thr  Gly  Glu  Tyr  Thr  Ile  Met  Thr  Ala  His  Phe  His  Leu  Lys  Arg  Lys
               245                      250                      255

Ile  Gly  Tyr  Phe  Val  Ile  Gln  Thr  Tyr  Leu  Pro  Cys  Ile  Met  Thr  Val
               260                      265                      270

Ile  Leu  Ser  Gln  Val  Ser  Phe  Trp  Leu  Asn  Arg  Glu  Ser  Val  Pro  Ala
          275                      280                      285

Arg  Thr  Val  Phe  Gly  Val  Thr  Thr  Val  Leu  Thr  Met  Thr  Thr  Leu  Ser
     290                      295                      300

Ile  Ser  Ala  Arg  Asn  Ser  Leu  Pro  Lys  Val  Ala  Tyr  Ala  Thr  Ala  Met
305                      310                      315                      320

Asp  Trp  Phe  Ile  Ala  Val  Cys  Tyr  Ala  Phe  Val  Phe  Ser  Ala  Leu  Ile
               325                      330                      335

Glu  Phe  Ala  Thr  Val  Asn  Tyr  Phe  Thr  Lys  Arg  Gly  Trp  Ala  Trp  Asp
               340                      345                      350

Gly  Lys  Lys  Ala  Leu  Glu  Ala  Ala  Lys  Ile  Lys  Lys  Arg  Glu  Val
          355                      360                      365

Ile  Leu  Asn  Lys  Ser  Thr  Asn  Ala  Phe  Thr  Thr  Gly  Lys  Met  Ser  His
     370                      375                      380

Pro  Pro  Asn  Ile  Pro  Lys  Glu  Gln  Thr  Pro  Ala  Gly  Thr  Ser  Asn  Thr
385                      390                      395                      400

Thr  Ser  Val  Ser  Val  Lys  Pro  Ser  Glu  Glu  Lys  Thr  Ser  Glu  Ser  Lys
               405                      410                      415

Lys  Thr  Tyr  Asn  Ser  Ile  Ser  Lys  Ile  Asp  Lys  Met  Ser  Arg  Ile  Val
               420                      425                      430

Phe  Pro  Val  Leu  Phe  Gly  Thr  Phe  Asn  Leu  Val  Tyr  Trp  Ala  Thr  Tyr
          435                      440                      445

Leu  Asn  Arg  Glu  Pro  Val  Ile  Lys  Gly  Ala  Ala  Ser  Pro  Lys
     450                      455                      460
```

( 2 ) INFORMATION FOR SEQ ID NO: 3:

(i) SEQUENCE CHARACTERISTICS:
    (A) LENGTH: 1408 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 27..1385

(xi) SEQUENCE DESCRIPTION: SEQ ID NO: 3:

```
AATTCTGCAT TTCAGTGCAC TGCAGG ATG GCG TCA TCT CTG CCC TGG CTG TGC         53
                             Met Ala Ser Ser Leu Pro Trp Leu Cys
                              1               5

ATT ATT CTG TGG CTA GAA AAT GCC CTA GGG AAA CTC GAA GTT GAA GGC         101
Ile Ile Leu Trp Leu Glu Asn Ala Leu Gly Lys Leu Glu Val Glu Gly
 10              15                  20                  25

AAC TTC TAC TCA GAA AAC GTC AGT CGG ATC CTG GAC AAC TTG CTT GAA         149
Asn Phe Tyr Ser Glu Asn Val Ser Arg Ile Leu Asp Asn Leu Leu Glu
             30                  35                  40

GGC TAT GAC AAT CGG CTG CGG CCG GGA TTT GGA GGT GCT GTC ACT GAA         197
Gly Tyr Asp Asn Arg Leu Arg Pro Gly Phe Gly Gly Ala Val Thr Glu
             45                  50                  55

GTC AAA ACA GAC ATT TAT GTG ACC AGT TTT GGG CCC GTG TCA GAT GTG         245
Val Lys Thr Asp Ile Tyr Val Thr Ser Phe Gly Pro Val Ser Asp Val
         60                  65                  70

GAG ATG GAG TAT ACG ATG GAT GTT TTT TTT CGC CAG ACC TGG ACT GAT         293
Glu Met Glu Tyr Thr Met Asp Val Phe Phe Arg Gln Thr Trp Thr Asp
     75                  80                  85

GAG AGG TTG AAG TTT GGG GGG CCA ACT GAG ATT CTG AGT CTG AAT AAT         341
Glu Arg Leu Lys Phe Gly Gly Pro Thr Glu Ile Leu Ser Leu Asn Asn
 90                  95                 100                 105

TTG ATG GTC AGT AAA ATC TGG ACG CCT GAC ACC TTT TTC AGA AAT GGT         389
Leu Met Val Ser Lys Ile Trp Thr Pro Asp Thr Phe Phe Arg Asn Gly
                 110                 115                 120

AAA AAG TCC ATT GCT CAC AAC ATG ACA ACT CCT AAT AAA CTC TTC AGA         437
Lys Lys Ser Ile Ala His Asn Met Thr Thr Pro Asn Lys Leu Phe Arg
                 125                 130                 135

ATA ATG CAG AAT GGA ACC ATT TTA TAC ACC ATG AGG CTT ACC ATC AAT         485
Ile Met Gln Asn Gly Thr Ile Leu Tyr Thr Met Arg Leu Thr Ile Asn
             140                 145                 150

GCT GAC TGT CCC ATG AGG CTG GTT AAC TTT CCT ATG GAT GGG CAT GCT         533
Ala Asp Cys Pro Met Arg Leu Val Asn Phe Pro Met Asp Gly His Ala
         155                 160                 165

TGT CCA CTC AAG TTT GGG AGC TAT GCT TAT CCC AAA AGT GAA ATC ATA         581
Cys Pro Leu Lys Phe Gly Ser Tyr Ala Tyr Pro Lys Ser Glu Ile Ile
170                 175                 180                 185

TAT ACG TGG AAA AAA GGA CCA CTT TAC TCA GTA GAA GTC CCA GAA GAA         629
Tyr Thr Trp Lys Lys Gly Pro Leu Tyr Ser Val Glu Val Pro Glu Glu
                 190                 195                 200

TCT TCA AGC CTT CTC CAG TAT GAT CTG ATT GGA CAA ACA GTA TCT AGT         677
Ser Ser Ser Leu Leu Gln Tyr Asp Leu Ile Gly Gln Thr Val Ser Ser
             205                 210                 215

GAG ACA ATT AAA TCT AAC ACA GGT GAA TAC GTT ATA ATG ACA GTT TAC         725
Glu Thr Ile Lys Ser Asn Thr Gly Glu Tyr Val Ile Met Thr Val Tyr
         220                 225                 230

TTC CAC TTG CAA AGG AAG ATG GGC TAC TTC ATG ATA CAG ATA TAC ACT         773
Phe His Leu Gln Arg Lys Met Gly Tyr Phe Met Ile Gln Ile Tyr Thr
     235                 240                 245
```

| | | | | | | | | | | | | | | | | |
|---|---|---|---|---|---|---|---|---|---|---|---|---|---|---|---|---|
| CCT | TGC | ATT | ATG | ACA | GTC | ATT | CTT | TCC | CAG | GTG | TCT | TTC | TGG | ATT | AAT | 821 |
| Pro | Cys | Ile | Met | Thr | Val | Ile | Leu | Ser | Gln | Val | Ser | Phe | Trp | Ile | Asn | |
| 250 | | | | 255 | | | | | 260 | | | | | 265 | | |
| AAG | GAG | TCC | GTC | CCA | GCA | AGA | ACT | GTT | CTT | GGG | ATC | ACC | ACT | GTT | TTA | 869 |
| Lys | Glu | Ser | Val | Pro | Ala | Arg | Thr | Val | Leu | Gly | Ile | Thr | Thr | Val | Leu | |
| | | | | 270 | | | | 275 | | | | | | 280 | | |
| ACT | ATG | ACC | ACT | TTG | AGC | ATC | AGT | GCC | CGG | CAC | TCT | TTG | CCA | AAA | GTG | 917 |
| Thr | Met | Thr | Thr | Leu | Ser | Ile | Ser | Ala | Arg | His | Ser | Leu | Pro | Lys | Val | |
| | | | 285 | | | | | 290 | | | | | 295 | | | |
| TCA | TAT | GCC | ACT | GCC | ATG | GAT | TGG | TTC | ATA | GCT | GTT | TGC | TTT | GCA | TTC | 965 |
| Ser | Tyr | Ala | Thr | Ala | Met | Asp | Trp | Phe | Ile | Ala | Val | Cys | Phe | Ala | Phe | |
| | | 300 | | | | 305 | | | | | 310 | | | | | |
| GTC | TTC | TCT | GCT | CTT | ATC | GAG | TTC | GCA | GCT | GTC | AAC | TAC | TTT | ACC | AAT | 1013 |
| Val | Phe | Ser | Ala | Leu | Ile | Glu | Phe | Ala | Ala | Val | Asn | Tyr | Phe | Thr | Asn | |
| | | 315 | | | | 320 | | | | | 325 | | | | | |
| CTT | CAG | ACA | CAG | AAG | GCG | AAA | AGG | AAG | GCA | CAG | TTT | GCA | GCC | CCA | CCC | 1061 |
| Leu | Gln | Thr | Gln | Lys | Ala | Lys | Arg | Lys | Ala | Gln | Phe | Ala | Ala | Pro | Pro | |
| 330 | | | | 335 | | | | | 340 | | | | | 345 | | |
| ACA | GTG | ACA | ATA | TCA | AAA | GCT | ACT | GAA | CCT | TTG | GAA | GCT | GAG | ATT | GTT | 1109 |
| Thr | Val | Thr | Ile | Ser | Lys | Ala | Thr | Glu | Pro | Leu | Glu | Ala | Glu | Ile | Val | |
| | | | | 350 | | | | | 355 | | | | | 360 | | |
| TTG | CAT | CCT | GAC | TCC | AAA | TAT | CAT | CTG | AAG | AAA | AGG | ATC | ACT | TCT | CTG | 1157 |
| Leu | His | Pro | Asp | Ser | Lys | Tyr | His | Leu | Lys | Lys | Arg | Ile | Thr | Ser | Leu | |
| | | | 365 | | | | 370 | | | | | 375 | | | | |
| TCT | TTG | CCA | ATA | GTT | TCA | TCT | TCC | GAG | GCC | AAT | AAA | GTG | CTC | ACG | AGA | 1205 |
| Ser | Leu | Pro | Ile | Val | Ser | Ser | Ser | Glu | Ala | Asn | Lys | Val | Leu | Thr | Arg | |
| | | 380 | | | | | 385 | | | | | 390 | | | | |
| GCG | CCC | ATC | TTA | CAA | TCA | ACA | CCT | GTC | ACA | CCC | CCA | CCA | CTC | CCG | CCA | 1253 |
| Ala | Pro | Ile | Leu | Gln | Ser | Thr | Pro | Val | Thr | Pro | Pro | Pro | Leu | Pro | Pro | |
| | 395 | | | | | 400 | | | | | 405 | | | | | |
| GCC | TTT | GGA | GGC | ACC | AGT | AAA | ATA | GAC | CAG | TAT | TCT | CGA | ATT | CTC | TTC | 1301 |
| Ala | Phe | Gly | Gly | Thr | Ser | Lys | Ile | Asp | Gln | Tyr | Ser | Arg | Ile | Leu | Phe | |
| 410 | | | | | 415 | | | | | 420 | | | | | 425 | |
| CCA | GTT | GCA | TTT | GCA | GGA | TTC | AAC | CTT | GTG | TAC | TGG | GTA | GTT | TAT | CTT | 1349 |
| Pro | Val | Ala | Phe | Ala | Gly | Phe | Asn | Leu | Val | Tyr | Trp | Val | Val | Tyr | Leu | |
| | | | | 430 | | | | | 435 | | | | | 440 | | |
| TCC | AAA | GAT | ACA | ATG | GAA | GTG | AGT | AGC | AGT | GTT | GAA | TAGCTTTTCC | | | | 1395 |
| Ser | Lys | Asp | Thr | Met | Glu | Val | Ser | Ser | Ser | Val | Glu | | | | | |
| | | | 445 | | | | | 450 | | | | | | | | |
| AGGACAACCT GAA | | | | | | | | | | | | | | | | 1408 |

(2) INFORMATION FOR SEQ ID NO: 4:

(i) SEQUENCE CHARACTERISTICS:
        (A) LENGTH: 453 amino acids
        (B) TYPE: amino acid
        (D) TOPOLOGY: linear (ii) MOLECULE TYPE: protein (xi) SEQUENCE DESCRIPTION: SEQ ID NO: 4:

| | | | | | | | | | | | | | | |
|---|---|---|---|---|---|---|---|---|---|---|---|---|---|---|
| Met | Ala | Ser | Ser | Leu | Pro | Trp | Leu | Cys | Ile | Ile | Leu | Trp | Leu | Glu | Asn |
| 1 | | | | 5 | | | | | 10 | | | | | 15 | |
| Ala | Leu | Gly | Lys | Leu | Glu | Val | Glu | Gly | Asn | Phe | Tyr | Ser | Glu | Asn | Val |
| | | | 20 | | | | | 25 | | | | | 30 | | |
| Ser | Arg | Ile | Leu | Asp | Asn | Leu | Leu | Glu | Gly | Tyr | Asp | Asn | Arg | Leu | Arg |
| | | | 35 | | | | 40 | | | | | 45 | | | |
| Pro | Gly | Phe | Gly | Gly | Ala | Val | Thr | Glu | Val | Lys | Thr | Asp | Ile | Tyr | Val |
| | | 50 | | | | | 55 | | | | | 60 | | | |
| Thr | Ser | Phe | Gly | Pro | Val | Ser | Asp | Val | Glu | Met | Glu | Tyr | Thr | Met | Asp |
| 65 | | | | | 70 | | | | | 75 | | | | | 80 |

```
Val Phe Phe Arg Gln Thr Trp Thr Asp Glu Arg Leu Lys Phe Gly Gly
                 85                  90                  95

Pro Thr Glu Ile Leu Ser Leu Asn Asn Leu Met Val Ser Lys Ile Trp
            100                 105                 110

Thr Pro Asp Thr Phe Phe Arg Asn Gly Lys Lys Ser Ile Ala His Asn
            115                 120                 125

Met Thr Thr Pro Asn Lys Leu Phe Arg Ile Met Gln Asn Gly Thr Ile
        130                 135                 140

Leu Tyr Thr Met Arg Leu Thr Ile Asn Ala Asp Cys Pro Met Arg Leu
145                 150                 155                 160

Val Asn Phe Pro Met Asp Gly His Ala Cys Pro Leu Lys Phe Gly Ser
                165                 170                 175

Tyr Ala Tyr Pro Lys Ser Glu Ile Ile Tyr Thr Trp Lys Lys Gly Pro
            180                 185                 190

Leu Tyr Ser Val Glu Val Pro Glu Glu Ser Ser Ser Leu Leu Gln Tyr
        195                 200                 205

Asp Leu Ile Gly Gln Thr Val Ser Ser Glu Thr Ile Lys Ser Asn Thr
        210                 215                 220

Gly Glu Tyr Val Ile Met Thr Val Tyr Phe His Leu Gln Arg Lys Met
225                 230                 235                 240

Gly Tyr Phe Met Ile Gln Ile Tyr Thr Pro Cys Ile Met Thr Val Ile
                245                 250                 255

Leu Ser Gln Val Ser Phe Trp Ile Asn Lys Glu Ser Val Pro Ala Arg
            260                 265                 270

Thr Val Leu Gly Ile Thr Thr Val Leu Thr Met Thr Thr Leu Ser Ile
        275                 280                 285

Ser Ala Arg His Ser Leu Pro Lys Val Ser Tyr Ala Thr Ala Met Asp
290                 295                 300

Trp Phe Ile Ala Val Cys Phe Ala Phe Val Phe Ser Ala Leu Ile Glu
305                 310                 315                 320

Phe Ala Ala Val Asn Tyr Phe Thr Asn Leu Gln Thr Gln Lys Ala Lys
                325                 330                 335

Arg Lys Ala Gln Phe Ala Ala Pro Pro Thr Val Thr Ile Ser Lys Ala
            340                 345                 350

Thr Glu Pro Leu Glu Ala Glu Ile Val Leu His Pro Asp Ser Lys Tyr
        355                 360                 365

His Leu Lys Lys Arg Ile Thr Ser Leu Ser Leu Pro Ile Val Ser Ser
        370                 375                 380

Ser Glu Ala Asn Lys Val Leu Thr Arg Ala Pro Ile Leu Gln Ser Thr
385                 390                 395                 400

Pro Val Thr Pro Pro Pro Leu Pro Pro Ala Phe Gly Gly Thr Ser Lys
                405                 410                 415

Ile Asp Gln Tyr Ser Arg Ile Leu Phe Pro Val Ala Phe Ala Gly Phe
            420                 425                 430

Asn Leu Val Tyr Trp Val Val Tyr Leu Ser Lys Asp Thr Met Glu Val
        435                 440                 445

Ser Ser Ser Val Glu
450
```

( 2 ) INFORMATION FOR SEQ ID NO: 5:

( i ) SEQUENCE CHARACTERISTICS:
        ( A ) LENGTH: 1866 base pairs
        ( B ) TYPE: nucleic acid
        ( C ) STRANDEDNESS: single ( D ) TOPOLOGY: linear ( i i ) MOLECULE TYPE: cDNA ( i x ) FEATURE:
    ( A ) NAME/KEY: CDS
    ( B ) LOCATION: 225..1646

( x i ) SEQUENCE DESCRIPTION: SEQ ID NO: 5:

```
GAATTCCGCG CGGGGAAGGG AAGAAGAGGA CGAGGTGGCG CAGAGACCGC GGGAGAACAC    60

AGTGCCTCCG GAGGAAATCT GCTCGGTCCC CGGCAGCCGC GCTTCCCCTT TGATGTTTTG   120

GTACGCCGTG GCCATGCGCC TCACATTAGA ATTACTGCAC TGGGCAGACT AAGTTGGATC   180

TCCTCTCTTC AGTGAAACCC TCAATTCCAT CAAAAACTAA AGGG ATG TGG AGA GTG   236
                                              Met Trp Arg Val
                                                1
```

```
CGG AAA AGG GGC TAC TTT GGG ATT TGG TCC TTC CCC TTA ATA ATC GCC    284
Arg Lys Arg Gly Tyr Phe Gly Ile Trp Ser Phe Pro Leu Ile Ile Ala
 5              10                  15                  20

GCT GTC TGT GCG CAG AGT GTC AAT GAC CCT AGT AAT ATG TCG CTG GTT    332
Ala Val Cys Ala Gln Ser Val Asn Asp Pro Ser Asn Met Ser Leu Val
                25                  30                  35

AAA GAG ACG GTG GAT AGA CTC CTG AAA GGC TAT GAC ATT CGT CTG AGA    380
Lys Glu Thr Val Asp Arg Leu Leu Lys Gly Tyr Asp Ile Arg Leu Arg
            40                  45                  50

CCA GAT TTT GGA GGT CCC CCC GTG GCT GTG GGG ATG AAC ATT GAC ATT    428
Pro Asp Phe Gly Gly Pro Pro Val Ala Val Gly Met Asn Ile Asp Ile
        55                  60                  65

GCC AGC ATC GAT ATG GTT TCT GAA GTC AAT ATG GAT TAT ACC TTG ACA    476
Ala Ser Ile Asp Met Val Ser Glu Val Asn Met Asp Tyr Thr Leu Thr
    70                  75                  80

ATG TAC TTT CAA CAA GCC TGG AGA GAT AAG AGG CTG TCC TAT AAT GTA    524
Met Tyr Phe Gln Gln Ala Trp Arg Asp Lys Arg Leu Ser Tyr Asn Val
 85                 90                  95                  100

ATA CCT TTA AAC TTG ACT CTG GAC AAC AGA GTG GCA GAC CAG CTC TGG    572
Ile Pro Leu Asn Leu Thr Leu Asp Asn Arg Val Ala Asp Gln Leu Trp
                105                 110                 115

GTG CCT GAT ACC TAT TTC CTG AAC GAT AAG AAG TCA TTT GTG CAC GGA    620
Val Pro Asp Thr Tyr Phe Leu Asn Asp Lys Lys Ser Phe Val His Gly
            120                 125                 130

GTG ACT GTT AAG AAC CGC ATG ATT CGC CTG CAT CCT GAT GGC ACC GTC    668
Val Thr Val Lys Asn Arg Met Ile Arg Leu His Pro Asp Gly Thr Val
        135                 140                 145

CTT TAT GGA CTC AGA ATC ACA ACC ACA GCT GCC TGC ATG ATG GAC CTA    716
Leu Tyr Gly Leu Arg Ile Thr Thr Thr Ala Ala Cys Met Met Asp Leu
    150                 155                 160

AGG AGG TAC CCA CTG GAT GAA CAA AAC TGC ACC TTG GAA ATT GAG AGC    764
Arg Arg Tyr Pro Leu Asp Glu Gln Asn Cys Thr Leu Glu Ile Glu Ser
165                 170                 175                 180

TAT GGA TAC ACA ACT GAT GAC ATT GAG TTT TAC TGG CGT GGC GAT GAT    812
Tyr Gly Tyr Thr Thr Asp Asp Ile Glu Phe Tyr Trp Arg Gly Asp Asp
                185                 190                 195

AAT GCA GTA ACA GGA GTA ACG AAA ATT GAA CTT CCA CAG TTC TCT ATT    860
Asn Ala Val Thr Gly Val Thr Lys Ile Glu Leu Pro Gln Phe Ser Ile
            200                 205                 210

GTA GAT TAC AAA CTT ATC ACC AAG AAG GTT GTT TTT TCC ACA GGT TCC    908
Val Asp Tyr Lys Leu Ile Thr Lys Lys Val Val Phe Ser Thr Gly Ser
        215                 220                 225

TAT CCC AGG TTA TCC CTC AGC TTT AAG CTT AAG AGA AAC ATT GGC TAC    956
Tyr Pro Arg Leu Ser Leu Ser Phe Lys Leu Lys Arg Asn Ile Gly Tyr
    230                 235                 240
```

```
TTT ATC CTG CAA ACA TAC ATG CCT TCC ATC CTG ATT ACC ATC CTC TCC    1004
Phe Ile Leu Gln Thr Tyr Met Pro Ser Ile Leu Ile Thr Ile Leu Ser
245                 250                 255                 260

TGG GTC TCC TTC TGG ATT AAT TAC GAT GCT TCA GCT GCA AGG GTG GCA    1052
Trp Val Ser Phe Trp Ile Asn Tyr Asp Ala Ser Ala Ala Arg Val Ala
                265                 270                 275

TTA GGA ATC ACA ACT GTC CTC ACA ATG ACC ACA ATC AAC ACC CAC CTC    1100
Leu Gly Ile Thr Thr Val Leu Thr Met Thr Thr Ile Asn Thr His Leu
            280                 285                 290

CGG GAA ACT CTC CCT AAA ATC CCC TAT GTG AAG GCC ATT GAC ATG TAC    1148
Arg Glu Thr Leu Pro Lys Ile Pro Tyr Val Lys Ala Ile Asp Met Tyr
        295                 300                 305

CTG ATG GGG TGC TTT GTC TTC GTT TTC ATG GCC CTT CTG GAA TAT GCC    1196
Leu Met Gly Cys Phe Val Phe Val Phe Met Ala Leu Leu Glu Tyr Ala
    310                 315                 320

CTA GTC AAC TAC ATC TTC TTT GGG AGG GGG CCC CAA CGC CAA AAG AAA    1244
Leu Val Asn Tyr Ile Phe Phe Gly Arg Gly Pro Gln Arg Gln Lys Lys
325                 330                 335                 340

GCA GCT GAG AAG GCT GCC AGT GCC AAC AAT GAG AAG ATG CGC CTG GAT    1292
Ala Ala Glu Lys Ala Ala Ser Ala Asn Asn Glu Lys Met Arg Leu Asp
                345                 350                 355

GTC AAC AAG ATG GAC CCC CAT GAG AAC ATC TTA CTG AGC ACT CTC GAG    1340
Val Asn Lys Met Asp Pro His Glu Asn Ile Leu Leu Ser Thr Leu Glu
            360                 365                 370

ATA AAA AAT GAA ATG GCC ACA TCT GAG GCT GTG ATG GGA CTT GGA GAC    1388
Ile Lys Asn Glu Met Ala Thr Ser Glu Ala Val Met Gly Leu Gly Asp
        375                 380                 385

CCC AGA AGC ACA ATG CTA GCC TAT GAT GCC TCC AGC ATC CAG TAT CGG    1436
Pro Arg Ser Thr Met Leu Ala Tyr Asp Ala Ser Ser Ile Gln Tyr Arg
    390                 395                 400

AAA GCT GGG TTG CCC AGG CAT AGT TTT GGC CGA AAT GCT CTG GAA CGA    1484
Lys Ala Gly Leu Pro Arg His Ser Phe Gly Arg Asn Ala Leu Glu Arg
405                 410                 415                 420

CAT GTG GCG CAA AAG AAA AGT CGC CTG AGG AGA CGC GCC TCC CAA CTG    1532
His Val Ala Gln Lys Lys Ser Arg Leu Arg Arg Arg Ala Ser Gln Leu
                425                 430                 435

AAA ATC ACC ATC CCT GAC TTG ACT GAT GTG AAT GCC ATA GAT CGG TGG    1580
Lys Ile Thr Ile Pro Asp Leu Thr Asp Val Asn Ala Ile Asp Arg Trp
            440                 445                 450

TCC CGC ATA TTC TTC CCA GTG GTT TTT TCC TTC TTC AAC ATC GTC TAT    1628
Ser Arg Ile Phe Phe Pro Val Val Phe Ser Phe Phe Asn Ile Val Tyr
    455                 460                 465

TGG CTT TAT TAT GTG AAC TAAAACATGG CCTCCCACTG GAAGCAAGGA           1676
Trp Leu Tyr Tyr Val Asn
470

CTAGATTCCT CCTCAAACCA GTTGTACAGC CTGATGTAGG ACTTGGAAAA CACATCAATC  1736

CAGGACAAAA GTGACGCTAA AATACCTTAG TTGCTGGCCT ATCCTGTGGT CCATTTCATA  1796

CCATTTGGGT TGCTTCTGCT AAGTAATGAA TACACTAAGG TCCTTGTGGT TTTCCAGTTA  1856

AAACGCAAGT                                                         1866
```

( 2 ) INFORMATION FOR SEQ ID NO: 6:

( i ) SEQUENCE CHARACTERISTICS:
        ( A ) LENGTH: 474 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

```
Met Trp Arg Val Arg Lys Arg Gly Tyr Phe Gly Ile Trp Ser Phe Pro
 1               5                   10                  15

Leu Ile Ile Ala Ala Val Cys Ala Gln Ser Val Asn Asp Pro Ser Asn
            20                  25              30

Met Ser Leu Val Lys Glu Thr Val Asp Arg Leu Leu Lys Gly Tyr Asp
        35              40                  45

Ile Arg Leu Arg Pro Asp Phe Gly Gly Pro Pro Val Ala Val Gly Met
    50              55                      60

Asn Ile Asp Ile Ala Ser Ile Asp Met Val Ser Glu Val Asn Met Asp
65              70                  75                      80

Tyr Thr Leu Thr Met Tyr Phe Gln Gln Ala Trp Arg Asp Lys Arg Leu
                85              90                      95

Ser Tyr Asn Val Ile Pro Leu Asn Leu Thr Leu Asp Asn Arg Val Ala
            100             105                 110

Asp Gln Leu Trp Val Pro Asp Thr Tyr Phe Leu Asn Asp Lys Lys Ser
        115             120                 125

Phe Val His Gly Val Thr Val Lys Asn Arg Met Ile Arg Leu His Pro
    130             135                 140

Asp Gly Thr Val Leu Tyr Gly Leu Arg Ile Thr Thr Thr Ala Ala Cys
145             150                 155                     160

Met Met Asp Leu Arg Arg Tyr Pro Leu Asp Glu Gln Asn Cys Thr Leu
            165                 170                 175

Glu Ile Glu Ser Tyr Gly Tyr Thr Thr Asp Asp Ile Glu Phe Tyr Trp
            180                 185                 190

Arg Gly Asp Asp Asn Ala Val Thr Gly Val Thr Lys Ile Glu Leu Pro
        195                 200                 205

Gln Phe Ser Ile Val Asp Tyr Lys Leu Ile Thr Lys Lys Val Val Phe
    210                 215                 220

Ser Thr Gly Ser Tyr Pro Arg Leu Ser Leu Ser Phe Lys Leu Lys Arg
225             230                 235                     240

Asn Ile Gly Tyr Phe Ile Leu Gln Thr Tyr Met Pro Ser Ile Leu Ile
            245                 250                 255

Thr Ile Leu Ser Trp Val Ser Phe Trp Ile Asn Tyr Asp Ala Ser Ala
            260                 265                 270

Ala Arg Val Ala Leu Gly Ile Thr Thr Val Leu Thr Met Thr Thr Ile
        275                 280                 285

Asn Thr His Leu Arg Glu Thr Leu Pro Lys Ile Pro Tyr Val Lys Ala
290                 295                 300

Ile Asp Met Tyr Leu Met Gly Cys Phe Val Phe Val Phe Met Ala Leu
305             310                 315                     320

Leu Glu Tyr Ala Leu Val Asn Tyr Ile Phe Phe Gly Arg Gly Pro Gln
            325                 330                 335

Arg Gln Lys Lys Ala Ala Glu Lys Ala Ala Ser Ala Asn Asn Glu Lys
        340                 345                 350

Met Arg Leu Asp Val Asn Lys Met Asp Pro His Glu Asn Ile Leu Leu
        355                 360                 365

Ser Thr Leu Glu Ile Lys Asn Glu Met Ala Thr Ser Glu Ala Val Met
    370                 375                 380

Gly Leu Gly Asp Pro Arg Ser Thr Met Leu Ala Tyr Asp Ala Ser Ser
385                 390                 395                 400

Ile Gln Tyr Arg Lys Ala Gly Leu Pro Arg His Ser Phe Gly Arg Asn
            405                 410                 415

Ala Leu Glu Arg His Val Ala Gln Lys Lys Ser Arg Leu Arg Arg Arg
```

|   | 420 |   |   |   |   | 425 |   |   |   |   | 430 |   |   |   |
|---|---|---|---|---|---|---|---|---|---|---|---|---|---|---|
| Ala | Ser | Gln | Leu | Lys | Ile | Thr | Ile | Pro | Asp | Leu | Thr | Asp | Val | Asn | Ala |
|   |   | 435 |   |   |   |   | 440 |   |   |   |   | 445 |   |   |

Ile Asp Arg Trp Ser Arg Ile Phe Phe Pro Val Val Phe Ser Phe Phe
    450             455             460

Asn Ile Val Tyr Trp Leu Tyr Tyr Val Asn
465             470

( 2 ) INFORMATION FOR SEQ ID NO: 7:

( i ) SEQUENCE CHARACTERISTICS:
      ( A ) LENGTH: 2189 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 214..1566

( x i ) SEQUENCE DESCRIPTION: SEQ ID NO: 7:

```
CCTAGCGCTC CTCTCCGGCT TCCACCAGCC CATCGCTCCA CGCTCTCTTG GCTGCTGCAG      60

TCTCGGTCTC TCTCTCTCTC TCTCTCTCTC TCTCTCTCTC TCTCTCTCTC TCTCTCTCTC     120

TCTCTCTCTC TCTCTCCCAA GTTTCCTATC TCGTCAAGAT CAGGGCAAAA GAAGAAAACA     180

CCGAATTCTG CTTGCCGTTT CAGAGCGGCG GTG ATG AAG ACA AAA TTG AAC ATC      234
                                      Met Lys Thr Lys Leu Asn Ile
                                       1               5

TAC AAC ATC GAG TTC CTG CTT TTT GTT TTC TTG GTG TGG GAC CCT GCC       282
Tyr Asn Ile Glu Phe Leu Leu Phe Val Phe Leu Val Trp Asp Pro Ala
        10              15              20

AGG TTG GTG CTG GCT AAC ATC CAA GAA GAT GAG GCT AAA AAT AAC ATT       330
Arg Leu Val Leu Ala Asn Ile Gln Glu Asp Glu Ala Lys Asn Asn Ile
    25              30              35

ACC ATC TTT ACG AGA ATT CTT GAC AGA CTT CTG GAT GGT TAC GAT AAT       378
Thr Ile Phe Thr Arg Ile Leu Asp Arg Leu Leu Asp Gly Tyr Asp Asn
 40              45              50              55

CGG CTT AGA CCA GGA CTG GGA GAC AGT ATT ACT GAA GTC TTC ACT AAC       426
Arg Leu Arg Pro Gly Leu Gly Asp Ser Ile Thr Glu Val Phe Thr Asn
            60              65              70

ATC TAC GTG ACC AGT TTT GGC CCT GTC TCA GAT ACA GAT ATG GAA TAT       474
Ile Tyr Val Thr Ser Phe Gly Pro Val Ser Asp Thr Asp Met Glu Tyr
        75              80              85

ACA ATT GAT GTT TTC TTT CGA CAA AAA TGG AAA GAT GAA CGT TTA AAA       522
Thr Ile Asp Val Phe Phe Arg Gln Lys Trp Lys Asp Glu Arg Leu Lys
        90              95              100

TTT AAA GGT CCT ATG AAT ATC CTT CGA CTA AAC AAT TTA ATG GCT AGC       570
Phe Lys Gly Pro Met Asn Ile Leu Arg Leu Asn Asn Leu Met Ala Ser
105             110             115

AAA ATC TGG ACT CCA GAT ACC TTT TTT CAC AAT GGG AAG AAA TCA GTA       618
Lys Ile Trp Thr Pro Asp Thr Phe Phe His Asn Gly Lys Lys Ser Val
120             125             130             135

GCT CAT AAT ATG ACA ATG CCA AAT AAG TTG CTT CGA ATT CAG GAT GAT       666
Ala His Asn Met Thr Met Pro Asn Lys Leu Leu Arg Ile Gln Asp Asp
            140             145             150

GGG ACT CTG CTG TAT ACC ATG AGG CTT ACA GTT CAA GCT GAA TGC CCA       714
Gly Thr Leu Leu Tyr Thr Met Arg Leu Thr Val Gln Ala Glu Cys Pro
            155             160             165

ATG CAC TTG GAG GAT TTC CCA ATG GAT GCT CAT TCA TGT CCT CTG AAA       762
```

```
Met His Leu Glu Asp Phe Pro Met Asp Ala His Ser Cys Pro Leu Lys
        170                 175                 180

TTT GGC AGC TAT GCA TAT ACA ACT TCA GAG GTC ACT TAT ATT TGG ACT    810
Phe Gly Ser Tyr Ala Tyr Thr Thr Ser Glu Val Thr Tyr Ile Trp Thr
    185                 190                 195

TAC AAT GCA TCT GAT TCA GTA CAG GTT GCT CCT GAT GGC TCT AGG TTA    858
Tyr Asn Ala Ser Asp Ser Val Gln Val Ala Pro Asp Gly Ser Arg Leu
200                 205                 210                 215

AAT CAA TAT GAC CTG CTG GGC CAA TCA ATC GGA AAG GAG ACA ATT AAA    906
Asn Gln Tyr Asp Leu Leu Gly Gln Ser Ile Gly Lys Glu Thr Ile Lys
                220                 225                 230

TCC AGT ACA GGT GAA TAT ACT GTA ATG ACA GCT CAT TTC CAC CTG AAA    954
Ser Ser Thr Gly Glu Tyr Thr Val Met Thr Ala His Phe His Leu Lys
            235                 240                 245

AGA AAA ATT GGG TAT TTT GTG ATT CAA ACC TAT CTG CCT TGC ATC ATG   1002
Arg Lys Ile Gly Tyr Phe Val Ile Gln Thr Tyr Leu Pro Cys Ile Met
        250                 255                 260

ACT GTC ATT CTC TCC CAA GTT TCA TTC TGG CTT AAC AGA GAA TCT GTG   1050
Thr Val Ile Leu Ser Gln Val Ser Phe Trp Leu Asn Arg Glu Ser Val
    265                 270                 275

CCT GCA AGA ACT GTG TTT GGA GTA ACA ACT GTC CTA ACA ATG ACA ACT   1098
Pro Ala Arg Thr Val Phe Gly Val Thr Thr Val Leu Thr Met Thr Thr
280                 285                 290                 295

CTA AGC ATC AGT GCT CGG AAT TCT CTC CCC AAA GTG GCT TAT GCA ACT   1146
Leu Ser Ile Ser Ala Arg Asn Ser Leu Pro Lys Val Ala Tyr Ala Thr
                300                 305                 310

GCC ATG GAC TGG TTT ATT GCT GTT TGT TAT GCA TTT GTG TTC TCT GCC   1194
Ala Met Asp Trp Phe Ile Ala Val Cys Tyr Ala Phe Val Phe Ser Ala
            315                 320                 325

CTA ATT GAA TTT GCA ACT GTT AAT TAC TTC ACC AAA AGA GGA TGG ACT   1242
Leu Ile Glu Phe Ala Thr Val Asn Tyr Phe Thr Lys Arg Gly Trp Thr
        330                 335                 340

TGG GAT GGG AAG AGT GTA GTA AAT GAC AAG AAA AAA GAA AAG GCT TCC   1290
Trp Asp Gly Lys Ser Val Val Asn Asp Lys Lys Lys Glu Lys Ala Ser
    345                 350                 355

GTT ATG ATA CAG AAC AAC GCT TAT GCA GTG GCT GTT GCC AAT TAT GCC   1338
Val Met Ile Gln Asn Asn Ala Tyr Ala Val Ala Val Ala Asn Tyr Ala
360                 365                 370                 375

CCG AAT CTT TCA AAA GAT CCA GTT CTC TCC ACC ATC TCC AAG AGT GCA   1386
Pro Asn Leu Ser Lys Asp Pro Val Leu Ser Thr Ile Ser Lys Ser Ala
                380                 385                 390

ACC ACG CCA GAA CCC AAC AAG AAG CCA GAA AAC AAG CCA GCT GAA GCA   1434
Thr Thr Pro Glu Pro Asn Lys Lys Pro Glu Asn Lys Pro Ala Glu Ala
            395                 400                 405

AAG AAA ACT TTC AAC AGT GTT AGC AAA ATT GAC AGA ATG TCC AGA ATA   1482
Lys Lys Thr Phe Asn Ser Val Ser Lys Ile Asp Arg Met Ser Arg Ile
        410                 415                 420

GTT TTT CCA GTT TTG TTT GGT ACC TTT AAT TTA GTT TAC TGG GCT ACA   1530
Val Phe Pro Val Leu Phe Gly Thr Phe Asn Leu Val Tyr Trp Ala Thr
    425                 430                 435

TAT TTA AAC AGA GAA CCT GTA TTA GGG GTC AGT CCT TGAATTGAGA        1576
Tyr Leu Asn Arg Glu Pro Val Leu Gly Val Ser Pro
440                 445                 450

CCCATGTTAT CTTTGGGATG TATAGCAACA TTAAATTTGG TTTGTTTTGC TATGTACAGT  1636

CTGACTAATA ACTGCTAATT TGTGATCCAA CATGTACAGT ATGTATATAG TGACATAGCT  1696

TACCAGTAGA CCTTTAATGG AGACATGCAT TTGCTAACTC ATGGAACTGC AGACAGAAAG  1756

CACTCCATGC GAAAACAGCC ATTGCCTTTT TTAAAGATTT ACCCTAGGAC CTGATTTAAA  1816

GTGAATTTCA AGTGACCTGA TTAATTTCCT ATTCTTCCAA ATGAGATGAA AATGGGGATC  1876
```

```
CTGTACAACC CTTTGTGGAC CCTTTTGGTT TAGCTCTTAA GTAGGGGTAT TTTCTACTGT  1936
TGCTTAATTA TGATGGAAGA TAACATTGTC ATTCCTAGAT GAATCCTTTG AAGTAACAAA  1996
CATTGTATCT GACATCAGCT CTGTTCATGA GTGCTCAGAG TCCCTGCTAA TGTAATTGGA  2056
AGCTTGGTAC ACATAAGAAA AACTAGAGAT TTGAAATCTA GCTATGAATT ACTCTATATA  2116
GTATCTATAG CCATGTACAT ATTACAGCAT GACAAGCTCG AAATAATTAT GAGTCAGCCC  2176
GAAAGATGTT AAT                                                    2189
```

( 2 ) INFORMATION FOR SEQ ID NO: 8:

( i ) SEQUENCE CHARACTERISTICS:
        ( A ) LENGTH: 451 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

```
Met Lys Thr Lys Leu Asn Ile Tyr Asn Ile Glu Phe Leu Leu Phe Val
 1               5                  10                  15

Phe Leu Val Trp Asp Pro Ala Arg Leu Val Leu Ala Asn Ile Gln Glu
                20                  25                  30

Asp Glu Ala Lys Asn Asn Ile Thr Ile Phe Thr Arg Ile Leu Asp Arg
            35                  40                  45

Leu Leu Asp Gly Tyr Asp Asn Arg Leu Arg Pro Gly Leu Gly Asp Ser
        50                  55                  60

Ile Thr Glu Val Phe Thr Asn Ile Tyr Val Thr Ser Phe Gly Pro Val
65                  70                  75                  80

Ser Asp Thr Asp Met Glu Tyr Thr Ile Asp Val Phe Phe Arg Gln Lys
                85                  90                  95

Trp Lys Asp Glu Arg Leu Lys Phe Lys Gly Pro Met Asn Ile Leu Arg
                100                 105                 110

Leu Asn Asn Leu Met Ala Ser Lys Ile Trp Thr Pro Asp Thr Phe Phe
            115                 120                 125

His Asn Gly Lys Lys Ser Val Ala His Asn Met Thr Met Pro Asn Lys
        130                 135                 140

Leu Leu Arg Ile Gln Asp Asp Gly Thr Leu Leu Tyr Thr Met Arg Leu
145                 150                 155                 160

Thr Val Gln Ala Glu Cys Pro Met His Leu Glu Asp Phe Pro Met Asp
                165                 170                 175

Ala His Ser Cys Pro Leu Lys Phe Gly Ser Tyr Ala Tyr Thr Thr Ser
                180                 185                 190

Glu Val Thr Tyr Ile Trp Thr Tyr Asn Ala Ser Asp Ser Val Gln Val
            195                 200                 205

Ala Pro Asp Gly Ser Arg Leu Asn Gln Tyr Asp Leu Leu Gly Gln Ser
        210                 215                 220

Ile Gly Lys Glu Thr Ile Lys Ser Ser Thr Gly Glu Tyr Thr Val Met
225                 230                 235                 240

Thr Ala His Phe His Leu Lys Arg Lys Ile Gly Tyr Phe Val Ile Gln
                245                 250                 255

Thr Tyr Leu Pro Cys Ile Met Thr Val Ile Leu Ser Gln Val Ser Phe
                260                 265                 270

Trp Leu Asn Arg Glu Ser Val Pro Ala Arg Thr Val Phe Gly Val Thr
            275                 280                 285

Thr Val Leu Thr Met Thr Thr Leu Ser Ile Ser Ala Arg Asn Ser Leu
```

|       |       |       |       |       |       | 290   |       |       |       |       |       | 295   |       |       |       |       |       | 300   |       |       |
|-------|-------|-------|-------|-------|-------|-------|-------|-------|-------|-------|-------|-------|-------|-------|-------|-------|-------|-------|-------|-------|

Pro Lys Val Ala Tyr Ala Thr Ala Met Asp Trp Phe Ile Ala Val Cys
305                     310                 315                 320

Tyr Ala Phe Val Phe Ser Ala Leu Ile Glu Phe Ala Thr Val Asn Tyr
                    325                 330                 335

Phe Thr Lys Arg Gly Trp Thr Trp Asp Gly Lys Ser Val Val Asn Asp
                340                 345                 350

Lys Lys Lys Glu Lys Ala Ser Val Met Ile Gln Asn Asn Ala Tyr Ala
            355                 360                 365

Val Ala Val Ala Asn Tyr Ala Pro Asn Leu Ser Lys Asp Pro Val Leu
        370                 375                 380

Ser Thr Ile Ser Lys Ser Ala Thr Thr Pro Glu Pro Asn Lys Lys Pro
385                 390                 395                 400

Glu Asn Lys Pro Ala Glu Ala Lys Lys Thr Phe Asn Ser Val Ser Lys
                405                 410                 415

Ile Asp Arg Met Ser Arg Ile Val Phe Pro Val Leu Phe Gly Thr Phe
                420                 425                 430

Asn Leu Val Tyr Trp Ala Thr Tyr Leu Asn Arg Glu Pro Val Leu Gly
            435                 440                 445

Val Ser Pro
450

(2) INFORMATION FOR SEQ ID NO: 9:

(i) SEQUENCE CHARACTERISTICS:
        (A) LENGTH: 1638 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 87..1562

(xi) SEQUENCE DESCRIPTION: SEQ ID NO: 9:

GAATTCCCTT GTTTCAGTTC ATTCATCCTT CTCTCCTTTC CGCTCAGACT GTAGAGCTCG   60

GTCTCTCCAA GTTTGTGCCT AAGAAG ATG ATA ATC ACA CAA ACA AGT CAC TGT   113
                                         Met Ile Ile Thr Gln Thr Ser His Cys
                                           1                 5

TAC ATG ACC AGC TTG GGA ATT CTT TTC CTG ATT AAT ATT CTC CCT GGA   161
Tyr Met Thr Ser Leu Gly Ile Leu Phe Leu Ile Asn Ile Leu Pro Gly
10                  15                  20                  25

ACC ACT GGT CAA GGG GAA TCA AGA CGA CAA GAA CCC GGG GAC TTT GTG   209
Thr Thr Gly Gln Gly Glu Ser Arg Arg Gln Glu Pro Gly Asp Phe Val
                30                  35                  40

AAG CAG GAC ATT GGC GGG CTG TCT CCT AAG CAT GCC CCA GAT ATT CCT   257
Lys Gln Asp Ile Gly Gly Leu Ser Pro Lys His Ala Pro Asp Ile Pro
            45                  50                  55

GAT GAC AGC ACT GAC AAC ATC ACT ATC TTC ACC AGA ATC TTG GAT CGT   305
Asp Asp Ser Thr Asp Asn Ile Thr Ile Phe Thr Arg Ile Leu Asp Arg
        60                  65                  70

CTT CTG GAC GGC TAT GAC AAC CGG CTG CGA CCT GGG CTT GGA GAT GCA   353
Leu Leu Asp Gly Tyr Asp Asn Arg Leu Arg Pro Gly Leu Gly Asp Ala
    75                  80                  85

GTG ACT GAA GTG AAG ACT GAC ATC TAC GTG ACC AGT TTT GGC CCT GTG   401
Val Thr Glu Val Lys Thr Asp Ile Tyr Val Thr Ser Phe Gly Pro Val
90                  95                  100                 105

-continued

| | | | | | | | | | | | | | | | | |
|---|---|---|---|---|---|---|---|---|---|---|---|---|---|---|---|---|
| TCA | GAC | ACT | GAC | ATG | GAG | TAC | ACT | ATT | GAT | GTA | TTT | TTT | CGG | CAG | ACA | 449 |
| Ser | Asp | Thr | Asp | Met 110 | Glu | Tyr | Thr | Ile 115 | Asp | Val | Phe | Phe | Arg | Gln 120 | Thr | |
| TGG | CAT | GAT | GAA | AGA | CTG | AAA | TTT | GAT | GGC | CCC | ATG | AAG | ATC | CTT | CCA | 497 |
| Trp | His | Asp | Glu 125 | Arg | Leu | Lys | Phe | Asp 130 | Gly | Pro | Met | Lys | Ile 135 | Leu | Pro | |
| CTG | AAC | AAT | CTC | CTG | GCT | AGT | AAG | ATC | TGG | ACA | CCG | GAC | ACC | TTC | TTC | 545 |
| Leu | Asn | Asn 140 | Leu | Leu | Ala | Ser | Lys 145 | Ile | Trp | Thr | Pro | Asp 150 | Thr | Phe | Phe | |
| CAC | AAT | GGC | AAG | AAA | TCA | GTG | GCT | CAT | AAC | ATG | ACC | ACG | CCC | AAC | AAG | 593 |
| His | Asn 155 | Gly | Lys | Lys | Ser | Val 160 | Ala | His | Asn | Met | Thr 165 | Thr | Pro | Asn | Lys | |
| CTG | CTC | AGA | TTG | GTG | GAC | AAC | GGA | ACC | CTC | CTC | TAT | ACA | ATG | AGG | TTA | 641 |
| Leu 170 | Leu | Arg | Leu | Val | Asp 175 | Asn | Gly | Thr | Leu | Leu 180 | Tyr | Thr | Met | Arg | Leu 185 | |
| ACA | ATT | CAT | GCT | GAG | TGT | CCC | ATG | CAT | TTG | GAA | GAT | TTT | CCC | ATG | GAT | 689 |
| Thr | Ile | His | Ala | Glu 190 | Cys | Pro | Met | His | Leu 195 | Glu | Asp | Phe | Pro | Met 200 | Asp | |
| GTG | CAT | GCC | TGC | CCA | CTG | AAG | TTT | GGA | AGC | TAT | GCC | TAT | ACA | ACA | GCT | 737 |
| Val | His | Ala | Cys 205 | Pro | Leu | Lys | Phe | Gly 210 | Ser | Tyr | Ala | Tyr | Thr 215 | Thr | Ala | |
| GAA | GTG | GTT | TAT | TCT | TGG | ACT | CTC | GGA | AAG | AAC | AAA | TCC | GTG | GAA | GTG | 785 |
| Glu | Val | Val 220 | Tyr | Ser | Trp | Thr | Leu 225 | Gly | Lys | Asn | Lys | Ser 230 | Val | Glu | Val | |
| GCA | CAG | GAT | GGT | TCT | CGC | TTG | AAC | CAG | TAT | GAC | CTT | TTG | GGC | CAT | GTT | 833 |
| Ala | Gln | Asp 235 | Gly | Ser | Arg | Leu | Asn 240 | Gln | Tyr | Asp | Leu | Leu 245 | Gly | His | Val | |
| GTT | GGG | ACA | GAG | ATA | ATC | CGG | TCT | AGT | ACA | GGA | GAA | TAT | GTC | GTC | ATG | 881 |
| Val 250 | Gly | Thr | Glu | Ile | Ile 255 | Arg | Ser | Ser | Thr | Gly 260 | Glu | Tyr | Val | Val | Met 265 | |
| ACA | ACC | CAC | TTC | CAT | CTC | AAG | CGA | AAA | ATT | GGC | TAC | TTT | GTG | ATC | CAG | 929 |
| Thr | Thr | His | Phe | His 270 | Leu | Lys | Arg | Lys | Ile 275 | Gly | Tyr | Phe | Val | Ile 280 | Gln | |
| ACC | TAC | TTG | CCA | TGT | ATC | ATG | ACT | GTC | ATT | CTG | TCA | CAA | GTG | TCG | TTC | 977 |
| Thr | Tyr | Leu | Pro 285 | Cys | Ile | Met | Thr | Val 290 | Ile | Leu | Ser | Gln | Val 295 | Ser | Phe | |
| TGG | CTC | AAC | AGA | GAG | TCT | GTT | CCT | GCC | CGT | ACA | GTC | TTT | GGT | GTC | ACC | 1025 |
| Trp | Leu | Asn 300 | Arg | Glu | Ser | Val | Pro 305 | Ala | Arg | Thr | Val | Phe 310 | Gly | Val | Thr | |
| ACT | GTG | CTT | ACC | ATG | ACC | ACC | TTG | AGT | ATC | AGT | GCC | AGA | AAT | TCC | TTA | 1073 |
| Thr | Val | Leu 315 | Thr | Met | Thr | Thr 320 | Leu | Ser | Ile | Ser | Ala 325 | Arg | Asn | Ser | Leu | |
| CCT | AAA | GTG | GCA | TAT | GCG | ACG | GCC | ATG | GAC | TGG | TTC | ATA | GCC | GTC | TGT | 1121 |
| Pro 330 | Lys | Val | Ala | Tyr | Ala 335 | Thr | Ala | Met | Asp | Trp 340 | Phe | Ile | Ala | Val | Cys 345 | |
| TAT | GCC | TTT | GTA | TTT | TCT | GCA | CTG | ATT | GAA | TTT | GCC | ACT | GTC | AAC | TAT | 1169 |
| Tyr | Ala | Phe | Val | Phe 350 | Ser | Ala | Leu | Ile | Glu 355 | Phe | Ala | Thr | Val | Asn 360 | Tyr | |
| TTC | ACC | AAG | CGG | AGT | TGG | GCT | TGG | GAA | GGC | AAG | AAG | GTG | CCA | GAG | GCC | 1217 |
| Phe | Thr | Lys | Arg 365 | Ser | Trp | Ala | Trp | Glu 370 | Gly | Lys | Lys | Val | Pro 375 | Glu | Ala | |
| CTG | GAG | ATG | AAG | AAG | AAA | ACA | CCA | GCA | GCC | CCA | GCA | AAG | AAA | ACC | AGC | 1265 |
| Leu | Glu | Met 380 | Lys | Lys | Lys | Thr | Pro 385 | Ala | Ala | Pro | Ala | Lys 390 | Lys | Thr | Ser | |
| ACT | ACC | TTC | AAC | ATC | GTG | GGG | ACC | ACC | TAT | CCC | ATC | AAC | CTG | GCC | AAG | 1313 |
| Thr | Thr 395 | Phe | Asn | Ile | Val | Gly 400 | Thr | Thr | Tyr | Pro | Ile 405 | Asn | Leu | Ala | Lys | |
| GAC | ACT | GAA | TTT | TCC | ACC | ATC | TCC | AAG | GGC | GCT | GCT | CCC | AGT | GCC | TCC | 1361 |
| Asp | Thr 410 | Glu | Phe | Ser | Thr | Ile 415 | Ser | Lys | Gly | Ala | Ala 420 | Pro | Ser | Ala | Ser 425 | |

| | | | | | | | | | | | | | | | | |
|---|---|---|---|---|---|---|---|---|---|---|---|---|---|---|---|---|
| TCA | ACC | CCA | ACA | ATC | ATT | GCT | TCA | CCC | AAG | GCC | ACC | TAC | GTG | CAG | GAC | 1409 |
| Ser | Thr | Pro | Thr | Ile | Ile | Ala | Ser | Pro | Lys | Ala | Thr | Tyr | Val | Gln | Asp | |
| | | | 430 | | | | | 435 | | | | | 440 | | | |
| AGC | CCG | ACT | GAG | ACC | AAG | ACC | TAC | AAC | AGT | GTC | AGC | AAG | GTT | GAC | AAA | 1457 |
| Ser | Pro | Thr | Glu | Thr | Lys | Thr | Tyr | Asn | Ser | Val | Ser | Lys | Val | Asp | Lys | |
| | | 445 | | | | | 450 | | | | | 455 | | | | |
| ATT | TCC | CGC | ATC | ATC | TTT | CCT | GTG | CTC | TTT | GCC | ATA | TTC | AAT | CTG | GTC | 1505 |
| Ile | Ser | Arg | Ile | Ile | Phe | Pro | Val | Leu | Phe | Ala | Ile | Phe | Asn | Leu | Val | |
| | | 460 | | | | 465 | | | | | 470 | | | | | |
| TAT | TGG | GCC | ACA | TAT | GTC | AAC | CGG | GAG | TCA | GCT | ATC | AAG | GGC | ATG | ATC | 1553 |
| Tyr | Trp | Ala | Thr | Tyr | Val | Asn | Arg | Glu | Ser | Ala | Ile | Lys | Gly | Met | Ile | |
| | 475 | | | | | 480 | | | | | 485 | | | | | |
| CGC | AAA | CAG | TAGATAGTGG | CAGTGCAGCA | ACCAGAGCAC | TGTATACCCC | | | | | | | | | | 1602 |
| Arg | Lys | Gln | | | | | | | | | | | | | | |
| 490 | | | | | | | | | | | | | | | | |

GTGAAGCATC CAGGCACCCA AACCCCGGGG CTCCCC    1638

( 2 ) INFORMATION FOR SEQ ID NO: 10:

( i ) SEQUENCE CHARACTERISTICS:
        ( A ) LENGTH: 492 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 10:

| | | | | | | | | | | | | | | |
|---|---|---|---|---|---|---|---|---|---|---|---|---|---|---|
| Met | Ile | Ile | Thr | Gln | Thr | Ser | His | Cys | Tyr | Met | Thr | Ser | Leu | Gly | Ile |
| 1 | | | | 5 | | | | | 10 | | | | | 15 | |
| Leu | Phe | Leu | Ile | Asn | Ile | Leu | Pro | Gly | Thr | Thr | Gly | Gln | Gly | Glu | Ser |
| | | | 20 | | | | | 25 | | | | | 30 | | |
| Arg | Arg | Gln | Glu | Pro | Gly | Asp | Phe | Val | Lys | Gln | Asp | Ile | Gly | Gly | Leu |
| | | 35 | | | | | 40 | | | | | 45 | | | |
| Ser | Pro | Lys | His | Ala | Pro | Asp | Ile | Pro | Asp | Asp | Ser | Thr | Asp | Asn | Ile |
| | 50 | | | | | 55 | | | | | 60 | | | | |
| Thr | Ile | Phe | Thr | Arg | Ile | Leu | Asp | Arg | Leu | Leu | Asp | Gly | Tyr | Asp | Asn |
| 65 | | | | | 70 | | | | | 75 | | | | | 80 |
| Arg | Leu | Arg | Pro | Gly | Leu | Gly | Asp | Ala | Val | Thr | Glu | Val | Lys | Thr | Asp |
| | | | | 85 | | | | | 90 | | | | | 95 | |
| Ile | Tyr | Val | Thr | Ser | Phe | Gly | Pro | Val | Ser | Asp | Thr | Asp | Met | Glu | Tyr |
| | | | 100 | | | | | 105 | | | | | 110 | | |
| Thr | Ile | Asp | Val | Phe | Phe | Arg | Gln | Thr | Trp | His | Asp | Glu | Arg | Leu | Lys |
| | | 115 | | | | | 120 | | | | | 125 | | | |
| Phe | Asp | Gly | Pro | Met | Lys | Ile | Leu | Pro | Leu | Asn | Asn | Leu | Leu | Ala | Ser |
| | 130 | | | | | 135 | | | | | 140 | | | | |
| Lys | Ile | Trp | Thr | Pro | Asp | Thr | Phe | Phe | His | Asn | Gly | Lys | Lys | Ser | Val |
| 145 | | | | | 150 | | | | | 155 | | | | | 160 |
| Ala | His | Asn | Met | Thr | Thr | Pro | Asn | Lys | Leu | Leu | Arg | Leu | Val | Asp | Asn |
| | | | | 165 | | | | | 170 | | | | | 175 | |
| Gly | Thr | Leu | Leu | Tyr | Thr | Met | Arg | Leu | Thr | Ile | His | Ala | Glu | Cys | Pro |
| | | | 180 | | | | | 185 | | | | | 190 | | |
| Met | His | Leu | Glu | Asp | Phe | Pro | Met | Asp | Val | His | Ala | Cys | Pro | Leu | Lys |
| | | 195 | | | | | 200 | | | | | 205 | | | |
| Phe | Gly | Ser | Tyr | Ala | Tyr | Thr | Thr | Ala | Glu | Val | Val | Tyr | Ser | Trp | Thr |
| | 210 | | | | | 215 | | | | | 220 | | | | |
| Leu | Gly | Lys | Asn | Lys | Ser | Val | Glu | Val | Ala | Gln | Asp | Gly | Ser | Arg | Leu |
| 225 | | | | | 230 | | | | | 235 | | | | | 240 |
| Asn | Gln | Tyr | Asp | Leu | Leu | Gly | His | Val | Val | Gly | Thr | Glu | Ile | Ile | Arg |

|     |     |     | 245 |     |     |     |     | 250 |     |     |     |     | 255 |     |     |
| --- | --- | --- | --- | --- | --- | --- | --- | --- | --- | --- | --- | --- | --- | --- | --- |

Ser Ser Thr Gly Glu Tyr Val Val Met Thr Thr His Phe His Leu Lys
            260                 265             270

Arg Lys Ile Gly Tyr Phe Val Ile Gln Thr Tyr Leu Pro Cys Ile Met
            275             280             285

Thr Val Ile Leu Ser Gln Val Ser Phe Trp Leu Asn Arg Glu Ser Val
        290             295             300

Pro Ala Arg Thr Val Phe Gly Val Thr Thr Val Leu Thr Met Thr Thr
305             310             315                         320

Leu Ser Ile Ser Ala Arg Asn Ser Leu Pro Lys Val Ala Tyr Ala Thr
                325             330             335

Ala Met Asp Trp Phe Ile Ala Val Cys Tyr Ala Phe Val Phe Ser Ala
            340             345             350

Leu Ile Glu Phe Ala Thr Val Asn Tyr Phe Thr Lys Arg Ser Trp Ala
        355             360             365

Trp Glu Gly Lys Lys Val Pro Glu Ala Leu Glu Met Lys Lys Lys Thr
    370             375             380

Pro Ala Ala Pro Ala Lys Lys Thr Ser Thr Thr Phe Asn Ile Val Gly
385             390             395                         400

Thr Thr Tyr Pro Ile Asn Leu Ala Lys Asp Thr Glu Phe Ser Thr Ile
            405             410             415

Ser Lys Gly Ala Ala Pro Ser Ala Ser Thr Pro Thr Ile Ile Ala
            420             425             430

Ser Pro Lys Ala Thr Tyr Val Gln Asp Ser Pro Thr Glu Thr Lys Thr
        435             440             445

Tyr Asn Ser Val Ser Lys Val Asp Lys Ile Ser Arg Ile Ile Phe Pro
    450             455             460

Val Leu Phe Ala Ile Phe Asn Leu Val Tyr Trp Ala Thr Tyr Val Asn
465             470             475                         480

Arg Glu Ser Ala Ile Lys Gly Met Ile Arg Lys Gln
            485             490

( 2 ) INFORMATION FOR SEQ ID NO: 11:

( i ) SEQUENCE CHARACTERISTICS:
        ( A ) LENGTH: 32 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 11:

AGCGCGCGTA ATACGACTCA CTATAGGGCG AA 32

( 2 ) INFORMATION FOR SEQ ID NO: 12:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 12:

CAGCATGAAT TGTTAACCTC ATTGTA 26

( 2 ) INFORMATION FOR SEQ ID NO: 13:

( i ) SEQUENCE CHARACTERISTICS:
    ( A ) LENGTH: 34 nucleotides
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 13:

ATTATTCAAG CTTGCCATGG ACAATGGAAT GCTC 34

( 2 ) INFORMATION FOR SEQ ID NO: 14:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 14:

GGTTTCCAGC TTACTTTGGA GAGGTAGC 28

( 2 ) INFORMATION FOR SEQ ID NO: 15:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 15:

GAGGAAGAAT TCAGGAGGGT GACCT 25

( 2 ) INFORMATION FOR SEQ ID NO: 16:

( i ) SEQUENCE CHARACTERISTICS:
        ( A ) LENGTH: 29 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 16:

GAAAATAACG AATTCCAGTG TCCAGCTTT 29

( 2 ) INFORMATION FOR SEQ ID NO: 17:

( i ) SEQUENCE CHARACTERISTICS:
        ( A ) LENGTH: 32 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 17:

CAAAAGAATT CAGCTGAGAA AGCTGCTAAT GC 32

( 2 ) INFORMATION FOR SEQ ID NO: 18:

( i ) SEQUENCE CHARACTERISTICS:
        ( A ) LENGTH: 34 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 18:

TCAGGCGAAT TCTCTTTTGT GCCACATGTC GTTC 34

( 2 ) INFORMATION FOR SEQ ID NO: 19:

( i ) SEQUENCE CHARACTERISTICS:
        ( A ) LENGTH: 32 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 19:

AGCGCGCGTA ATACGACTCA CTATAGGGCG AA 32

( 2 ) INFORMATION FOR SEQ ID NO: 20:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 20:

CATCCAGTGG GTACCTCCTT AGGT 24

( 2 ) INFORMATION FOR SEQ ID NO: 21:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 21:

GCAATGAAAA TCCGGACTGG CAT 23

( 2 ) INFORMATION FOR SEQ ID NO: 22:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 22:

GGGAGGGAAG CTTCTGCAAC CAAGAGGC 28

( 2 ) INFORMATION FOR SEQ ID NO: 23:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 23:

```
ACCACATAGA  AGCTTATTTA  AGTGGAC           27
```

( 2 ) INFORMATION FOR SEQ ID NO: 24:

( i ) SEQUENCE CHARACTERISTICS:
        ( A ) LENGTH: 33 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 24:

```
TAATCAAGCT  TAGTAATGTG  GACAGTACAA  AAT      33
```

( 2 ) INFORMATION FOR SEQ ID NO: 25:

( i ) SEQUENCE CHARACTERISTICS:
        ( A ) LENGTH: 33 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 25:

```
AAATGGAAGC  TTTAGAACAG  ACCTCAGTGT  ACA      33
```

STABLY TRANSFECTED RODENT FIBROBLAST CELL LINES EXPRESSING HUMAN GABA-$_A$-RECEPTORS

This invention concerns a cell line, and in particular relates to a stable cell line capable of expressing human or animal GABA$_A$ receptors. The invention further concerns the cloning of novel cDNA sequences encoding particular subunits of the human GABA$_A$ receptor. In addition, the invention relates to the use of the cell line in a screening technique for the design and development of subtype-specific medicaments.

Gamma-amino butyric acid (GABA) is a major inhibitory neurotransmitter in the central nervous system. It mediates fast synaptic inhibition by opening the chloride channel intrinsic to the GABA$_A$ receptor. This receptor comprises a multimeric protein of molecular size 230–270 kDa with specific binding sites for a variety of drugs including benzodiazepines, barbiturates and β-carbolines, in addition to sites for the agonist ligand GABA (for reviews see Stephenson, Biochem. J., 1988, 249, 21; Olsen and Tobin, Faseb J., 1990, 4, 1469; and Sieghart, Trends in Pharmacol. Sci., 1989, 10, 407).

Molecular biological studies demonstrate that the receptor is composed of several distinct types of subunit, which are divided into four classes ($\alpha$, $\beta$, $\gamma$, and $\delta$) based on their sequence similarities. To date, six types of $\alpha$ (Schofield et al., Nature (London), 1987, 328, 221; Levitan et al., Nature (London), 1988, 335, 76; Ymer et al., EMBO J., 1989, 8, 1665; Pritchett & Seeberg, J. Neurochem., 1990, 54, 802; Luddens et al., Nature (London), 1990, 346, 648; and Khrestchatisky et al., Neuron, 1989, 3, 745), three types of β (Ymer et al., EMBO J., 1989, 8, 1665), two types of $\gamma$ (Ymer et al., EMBO J., 1990, 9, 3261; and Shivers et al., Neuron, 1989, 3, 327) and one $\delta$ subunit (Shivers et al., Neuron, 1989, 3, 327) have been identified.

The differential distribution of many of the subunits has been characterised by in situ hybridisation (Sequier et al., Proc. Natl. Acad. Sci. USA, 1988, 85, 7815; Malherbe et al., J. Neurosci., 1990, 10, 2330; and Shivers et al., Neuron, 1989, 3, 327) and this has permitted it to be speculated which subunits, by their co-localisation, could theoretically exist in the same receptor complex.

Various combinations of subunits have been co-transfected into cells to identify synthetic combinations of subunits whose pharmacology parallels that of bona fide GABA$_A$ receptors in vivo (Pritchett et al., Science, 1989, 245, 1389; Malherbe et al., J. Neurosci., 1990, 10, 2330; Pritchett and Seeberg, J. Neurochem., 1990, 54, 1802; and Luddens et al., Nature (London), 1990, 346, 648). This approach has revealed that, in addition to an $\alpha$ and β subunit, either $\gamma_1$ or $\gamma_2$ (Pritchett et al., Nature (London), 1989, 338, 582; Ymer et al., EMBO J., 1990, 9, 3261; and Malherbe et al., J. Neurosci., 1990, 10, 2330) or $\gamma_3$ (Herb et al., Proc. Natl. Acad. Sci. USA, 1992, 89, 1433; Knoflach et al., FEBS Lett., 1991, 293, 191; and Wilson-Shaw et al., FEBS Lett., 1991, 284, 211) is also generally required to confer benzodiazepine sensitivity, and that the benzodiazepine pharmacology of the expressed receptor is largely dependent on the identity of the $\alpha$ and $\gamma$ subunits present. Receptors containing a $\delta$ subunit (i.e. $\alpha\beta\delta$) do not appear to bind benzodiazepines (Shivers et al., Neuron, 1989, 3, 327). Combinations of subunits have been identified which exhibit the pharmacological profile of a BZ$_1$ type receptor ($\alpha_1\beta_1\gamma_2$) and a BZ$_2$ type receptor ($\alpha_2\beta_1\gamma_2$ or $\alpha_3\beta_1\gamma_2$, Pritchett et al., Nature (London), 1989, 338, 582), as well as two GABA$_A$ receptors with a novel pharmacology, $\alpha_5\beta_2\gamma_2$ (Pritchett and Seeberg, J. Neurochem., 1990, 54, 1802) and $\alpha_6\beta_2\gamma_2$ (Luddens et al., Nature (London), 1990, 346, 648). Although the pharmacology of these expressed receptors appears similar to that of those identified in brain tissue by radioligand binding, it has nonetheless not been shown that these receptor subunit combinations exist in vivo.

FIG. 2 shows the nucleotide sequence (SEQ ID NO:7) and deduced amino acid sequence (SED ID NO:8) encoding the human GABA$_A$ receptor $\alpha_2$ subunit.

FIG. 3 shows the nucleotide sequence (SEQ ID NO:9) and deduced amino acid sequence (SEQ ID NO:10) encoding the human GABA$_A$ receptor $\alpha_3$ subunit.

FIG. 4 shows the nucleotide sequence (SEQ ID NO:1) and deduced amino acid sequence (SEQ ID NO:2) encoding the human GABA$_A$ receptor $\alpha_5$ subunit.

FIG. 5 shows the nucleotide sequence (SEQ ID NO:3) and deduced amino acid sequence (SEQ ID NO:4) encoding the human GABA$_A$ receptor $\alpha_6$ subunit.

FIG. 6 shows the nucleotide sequence (SEQ ID NO:5) and deduced amino acid sequence (SEQ ID NO:6) encoding the human GABA$_A$ receptor $\beta_2$ subunit.

Figure 1:
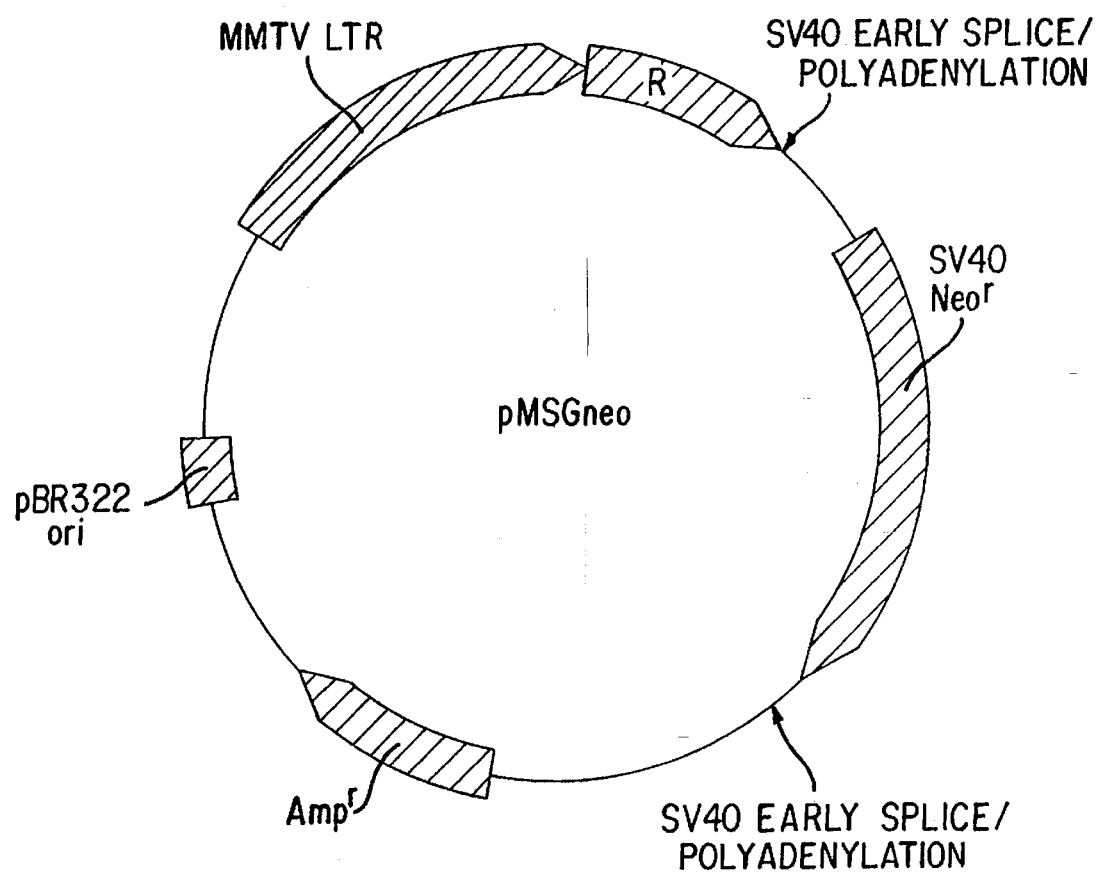
FIG. 1 shows the DNA plasmid expression vector pMS-Gneo. The designation "R" represents the nucleotide sequence of a given alpha, beta or gamma subunit of the GABA$_A$ receptor, fused downstream of the inducible MMTV-LTR promoter fragment.

The present invention is concerned with the production of permanently transfected cells containing the GABA$_A$ receptor, which will be useful for screening for drugs which act on this receptor. The GABA$_A$ receptor has previously been expressed in Xenopus oocytes (Sigel et al., Neuron, 1990, 5, 703–711) and in transiently transfected mammalian cells (Pritchett et al., Science, 1989, 245, 1389–1392). However, both of those systems involve transient expression and are unsuitable for screening purposes.

We have now achieved the stable expression of the receptor.

Accordingly, the present invention provides a stably co-transfected eukaryotic cell line capable of expressing a GABA$_A$ receptor, which receptor comprises at least one alpha, one beta and one gamma subunit.

This has been achieved by co-transfecting cells with three expression vectors, each harbouring cDNAs encoding for an $\alpha$, β or $\gamma$ GABA$_A$ receptor subunit. In a further aspect, therefore, the present invention provides a process for the preparation of a eukaryotic cell line capable of expressing a GABA$_A$ receptor, which comprises stably co-transfecting a eukaryotic host cell with at least three expression vectors, one such vector harbouring the cDNA sequence encoding for an alpha, another such vector harbouring the cDNA sequence encoding for a beta, and a third such vector harbouring the cDNA sequence encoding for a gamma GABA$_A$ receptor subunit. The stable cell-line which is established expresses an $\alpha\beta\gamma$ GABA$_A$ receptor. Each receptor thereby expressed, comprising a unique combination of $\alpha$, β and $\gamma$ subunits, will be referred to hereinafter as a GABA$_A$ receptor "subunit combination". Pharmacological and electrophysiological data confirm that the recombinant $\alpha\beta\gamma$ receptor expressed by the cells of the present invention has the properties expected of a native GABA$_A$ receptor.

Expression of the GABA$_A$ receptor may be accomplished by a variety of different promoter-expression systems in a variety of different host cells. The eukaryotic host cells suitably include yeast, insect and mammalian cells. Preferably the eukaryotic cells which can provide the host for the expression of the receptor are mammalian cells. Suitable host cells include rodent fibroblast lines, for example mouse Ltk⁻, Chinese hamster ovary (CHO) and baby hamster kidney (BHK); HeLa; and HEK293 cells. It is necessary to incorporate at least one $\alpha$, one $\beta$ and one $\gamma$ subunit into the cell line in order to produce the required receptor. Within this limitation, the choice of receptor subunit combination is made according to the type of activity or selectivity which is being screened for. For example, benzodiazepines (designated BZ) represent one class of drugs which act upon the $GABA_A$ receptor. The presence of an $\alpha_1$ subunit is specific for a class of benzodiazepines having the pharmacology designated $BZ_1$; whereas $\alpha_2$ to $\alpha_5$ define different pharmacological profiles, broadly designated as $BZ_2$. The type of $\beta$ subunit is not critical in defining the class of benzodiazepine, although a $\beta$ subunit is required. The $\gamma$ subunit is also important in defining BZ selectivity. It is likely that differentiation between $\alpha$ subunit selectivity is conferred by the identity of the particular $\gamma$ subunit present.

In order to employ this invention most effectively for screening purposes, it is preferable to build up a library of cell lines, each with a different combination of subunits. Typically a library of 5 or 6 cell line types is convenient for this purpose. Preferred subunit combinations include: $\alpha_1\beta_1\gamma_2$; $\alpha_1\beta_2\gamma_2$; $\alpha_2\beta_1\gamma_1$; $\alpha_2\beta_1\gamma_2$; $\alpha_2\beta_1\gamma_3$; $\alpha_3\beta_1\gamma_2$; $\alpha_3\beta_1\gamma_3$; $\alpha_4\beta_1\gamma_2$; $\alpha_5\beta_1\gamma_2$; and $\alpha_6\beta_1\gamma_2$; especially $\alpha_1\beta_1\gamma_{2L}$.

In a particular embodiment, the present invention provides a stably co-transfected eukaryotic cell line capable of expressing a human $GABA_A$ receptor comprising the $\alpha_1\beta_3\gamma_2$ subunit combination.

In a further embodiment, the present invention provides a stably co-transfected eukaryotic cell line capable of expressing a human $GABA_A$ receptor comprising the $\alpha_2\beta_3\gamma_2$ subunit combination.

In a still further embodiment, the present invention provides a stably co-transfected eukaryotic cell line capable of expressing a human $GABA_A$ receptor comprising the $\alpha_5\beta_3\gamma_2$ subunit combination.

In yet further embodiments, the present invention provides stably co-transfected eukaryotic cell lines capable of expressing human $GABA_A$ receptors comprising the $\alpha_1\beta_1\gamma_{2S}$, $\alpha_1\beta_2\gamma_2$, $\alpha_3\beta_3\gamma_2$ and $\alpha_6\beta_3\gamma_2$ subunit combinations.

The DNAs for the receptor subunits can be obtained from known sources, and are generally obtained as specific nucleotide sequences harboured by a standard cloning vector such as those described, for example, by Maniatis et al. in *Molecular Cloning, A Laboratory Manual*, Cold Spring Harbor Press, New York, 2nd edition, 1989. Preferably the cDNA sequences are derived from the human gene. However, for screening purposes, cDNAs from other species are also suitable, such as bovine or rat DNA. Known sources of $GABA_A$ receptor subunit cDNAs are as follows:

| Subunit | Reference |
|---|---|
| $\beta_1^1$ bovine, $\beta_1$ bovine | Schofield et al., Nature, 1987, 328, 221–227. |
| $\beta_1^1$ human, $\beta_1$ human | Schofield et al., FEBS Lett., 1989, 244, 361–364. |
| $\alpha_2$ rat | Khrestchatisky et al., J. Neurochem., 1991, 56, 1717. |
| $\alpha_2$ bovine, $\alpha_3$ bovine | Levitan et al., Nature, 1988, 335, 76–79. |
| $\alpha_4$ rat | Wisden et al., FEBS Lett., 1991, 289, 227. |
| $\alpha_4$ bovine | Ymer et al., FEBS Lett., 1989, 258, 119–122. |
| $\alpha_5$ rat | Pritchett and Seeburg, J. Neurochem., 1990, 54, 1802–1804. |
| $\alpha_6$ rat, $\alpha_6$ bovine | Luddens et al., Nature, 1990, 346, 648–651. |
| $\beta_2$ bovine, $\beta_2$ rat, $\beta_3$ bovine, $\beta_3$ rat | Ymer et al., EMBO J., 1989, 8, 1665–1670. |
| $\beta_3$ human | Wagstaff et al., Am. J. Hum. Genet., 1991, 49, 330. |
| $\gamma_1$ human, $\gamma_1$ rat, $\gamma_1$ bovine | Ymer et al., EMBO J., 1990, 9, 3261–3267. |
| $\gamma_2$ human | Pritchett et al., Nature, 1989, 338, 582–585. |
| $\gamma_2$ bovine | Whiting et al., Proc. Natl. Acad. Sci. USA, 1990, 57, 9966–9970. |
| $\gamma_3$ rat | Herb et al., Proc. Natl. Acad. Sci. USA, 1992, 89, 1433; and Knoflach et al., FEBS Lett., 1991, 293, 191. |
| $\gamma_3$ mouse | Wilson-Shaw et al., FEBS Lett., 1991, 284, 211. |
| $\delta$ rat | Shivers et al., Neuron, 1989, 3, 327. |

Certain cDNA sequences encoding various subunits of the human $GABA_A$ receptor have hitherto been unavailable. These include in particular the sequences encoding the $\alpha_2$, $\alpha_3$, $\alpha_5$, $\alpha_6$ and $\beta_2$ subunits, which nucleotide sequences are accordingly novel. We have now ascertained the cDNA sequences of the $\alpha_2$, $\alpha_3$, $\alpha_5$, $\alpha_6$ and $\beta_2$ subunits of the human $GABA_A$ receptor. These nucleotide sequences, together with the deduced amino acid sequences corresponding thereto, are depicted in FIGS. 2 to 6 of the accompanying drawings. The present invention accordingly provides in several additional aspects DNA molecules encoding the $\alpha_2$, $\alpha_3$, $\alpha_5$, $\alpha_6$ and $\beta_2$ subunits of the human $GABA_A$ receptor comprising all or a portion of the sequences depicted in FIGS. 2, 3, 4, 5 and 6 respectively, or substantially similar sequences.

The sequencing of the novel cDNA molecules in accordance with the invention can conveniently be carried out by the standard procedure described in accompanying Example 3; or may be accomplished by alternative molecular cloning techniques which are well known in the art, such as those described by Maniatis et al. in *Molecular Cloning, A Laboratory Manual*, Cold Spring Harbor Press, New York, 2nd edition, 1989.

In another aspect, the invention provides a recombinant expression vector comprising the nucleotide sequence of a $GABA_A$ receptor subunit together with additional sequences capable of directing the synthesis of the said $GABA_A$ receptor subunit in cultures of stably co-transfected eukaryotic cells.

The term "expression vectors" as used herein refers to DNA sequences that are required for the transcription of cloned copies of recombinant DNA sequences or genes and the translation of their mRNAs in an appropriate host. Such vectors can be used to express eukaryotic genes in a variety of hosts such as bacteria, blue-green algae, yeast cells, insect cells, plant cells and animal cells. Specifically designed vectors allow the shuttling of DNA between bacteria-yeast, bacteria-plant or bacteria-animal cells. An appropriately constructed expression vector should contain: an origin of replication for autonomous replication in host cells, selective markers, a limited number of useful restriction enzyme sites, a high copy number, and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

The term "cloning vector" as used herein refers to a DNA molecule, usually a small plasmid or bacteriophage DNA capable of self-replication in a host organism, and used to introduce a fragment of foreign DNA into a host cell. The foreign DNA combined with the vector DNA constitutes a recombinant DNA molecule which is derived from recombinant technology. Cloning vectors may include plasmids, bacteriophages, viruses and cosmids.

The recombinant expression vector in accordance with the invention may be prepared by inserting the nucleotide sequence of the chosen $GABA_A$ subunit into a suitable precursor expression vector (hereinafter referred to as the "precursor vector") using conventional recombinant DNA methodology known from the art. The precursor vector may be obtained commercially, or constructed by standard techniques from known expression vectors. The precursor vector suitably contains a selection marker, typically an antibiotic resistance gene, such as the neomycin or ampicillin resistance gene. The precursor vector preferably contains a neomycin resistance gene, adjacent the SV40 early splicing and polyadenylation region; an ampicillin resistance gene; and an origin of replication, e.g. pBR322 ori. The vector also preferably contains an inducible promoter, such as MMTV-LTR (inducible with dexamethasone) or metallothionin (inducible with zinc), so that transcription can be controlled in the cell line of this invention. This reduces or avoids any problem of toxicity in the cells because of the chloride channel intrinsic to the $GABA_A$ receptor.

One suitable precursor vector is pMAMneo, available from Clontech Laboratories Inc. (Lee et al., *Nature*, 1981, 294, 228; and Sardet et al., *Cell*, 1989, 56, 271). Alternatively the precursor vector pMSGneo can be constructed from the vectors pMSG and pSV2neo as described in Example 1 herein.

The recombinant expression vector of the present invention is then produced by cloning the $GABA_A$ receptor subunit cDNA into the above precursor vector. The required receptor subunit cDNA is subcloned from the vector in which it is harboured, and ligated into a restriction enzyme site, e.g. the HindIII site, in the polylinker of the precursor vector, for example pMAMneo or pMSGneo, by standard cloning methodology known from the art, and in particular by techniques analogous to those described in Example 1, step (b) herein. Before this subcloning, it is often advantageous, in order to improve expression, to modify the end of a subunit cDNA with additional 5' untranslated sequences, for example by modifying the 5' end of the $\gamma_{2L}$ subunit DNA by addition of 5' untranslated region sequences from the $\alpha_1$ subunit DNA.

One suitable expression vector of the present invention is illustrated in FIG. 1 of the accompanying drawings, in which R represents the nucleotide sequence of a given alpha, beta or gamma subunit of the $GABA_A$ receptor, and the remainder of the expression vector depicted therein is derived from the precursor vector pMSGneo and constructed as described in accompanying Example 1, steps (a) and (b).

For each cell line of the present invention, three such vectors will be necessary, one containing an $\alpha$ subunit, one containing a $\beta$ subunit, and the third containing a $\gamma$ subunit.

Cells are then co-transfected with the desired combination of three expression vectors. There are several commonly used techniques for transfection of eukaryotic cells in vitro. Calcium phosphate precipitation of DNA is most commonly used (Bachetti et al., *Proc. Natl. Acad. Sci. USA*, 1977, 74, 1590–1594; Maitland et al., *Cell*, 1977, 14, 133–141), and represents a favoured technique in the context of the present invention.

A small percentage of the host cells takes up the recombinant DNA. In a small percentage of those, the DNA will integrate into the host cell chromosome. Because the neomycin resistance gene will have been incorporated into these host cells, they can be selected by isolating the individual clones which will grow in the presence of neomycin. Each such clone is then tested to. identify those which will produce the receptor. This is achieved by inducing the production, for example with dexamethasone, and then detecting the presence of receptor by means of radioligand binding.

In a further aspect, the present invention provides protein preparations of $GABA_A$ receptor subunit combinations, especially human $GABA_A$ receptor subunit combinations, derived from cultures of stably transfected eukaryotic cells. The invention also provides preparations of membranes containing subunit combinations of the $GABA_A$ receptor, especially human $GABA_A$ receptor subunit combinations, derived from cultures of stably transfected eukaryotic cells. In particular, the protein preparations and membrane preparations according to the invention will suitably contain the $\alpha_1\beta_1\gamma_{2L}$, $\alpha_1\beta_3\gamma_2$, $\alpha_2\beta_{31}\gamma_2$, $\alpha_5\beta_3\gamma_2$, $\alpha_1\beta_1\gamma_{2S}$, $\alpha_1\beta_2\gamma_2$, $\alpha_3\beta_3\gamma_2$ or $\alpha_6\beta_3\gamma_2$ subunit combinations of the human $GABA_A$ receptor, and will preferably contain a human $GABA_A$ receptor consisting of the $\alpha_1\beta_1\gamma_{2L}$, $\alpha_1\beta_3\gamma_{2S}$, $\alpha_2\beta_3\gamma_{2S}$, $\alpha_5\beta_3\gamma_{2S}$, $\alpha_1\beta_1\gamma_{2S}$, $\alpha_1\beta_2\gamma_{2S}$, $\alpha_3\beta_3\gamma_{2S}$ or $\alpha_6\beta_3\gamma_{2S}$ subunit combinations. In an especially preferred embodiment, the invention provides cell membranes containing a human $GABA_A$ receptor consisting of the $\alpha_1\beta_1\gamma_{2L}$, $\alpha_1\beta_3\gamma_{2S}$, $\alpha_2\beta_3\gamma_{2S}$, $\alpha_5\beta_3\gamma_{2S}$, $\alpha_1\beta_1\gamma_{2S}$, $\alpha_1\beta_2\gamma_{2S}$, $\alpha_3\beta_3\gamma_{2S}$, or $\alpha_6\beta_3\gamma_{2S}$ subunit combinations isolated from stably transfected mouse Ltk$^-$ fibroblast cells.

The cell line, and the membrane preparations therefrom, according to the present invention have utility in screening and design of drugs which act upon the $GABA_A$ receptor, for example benzodiazepines, barbiturates, $\beta$-carbolines and neurosteroids. The present invention accordingly provides the use of the cell line described above, and membrane preparations derived therefrom, in screening for and designing medicaments which act upon the $GABA_A$ receptor. Of particular interest in this context are molecules capable of interacting selectively with $GABA_A$ receptors made up of varying subunit combinations. As will be readily apparent, the cell line in accordance with the present invention, and the membrane preparations derived therefrom, provide ideal systems for the study of structure, pharmacology and function of the various $GABA_A$ receptor subtypes.

The following non-limiting Examples illustrate the present invention.

EXAMPLE 1

PREPARATION OF $\alpha_1\beta_1\gamma_{2L}$ TRANSFECTED CELLS a) Construction of eukaryotic expression vector pMSGneo The approx. 2500 base pair HindIII-EcoRI fragment of the vector pMSG (purchased from Pharmacia Biosystems Limited, Milton Keynes, United Kingdom), containing the gpt structural gene and SV40 polyadenylation signals was replaced by the approx. 2800 base pair HindIII-EcoRI fragment of pSV2neo (Southern, P. J. and Berg, P. J., *Molecular and Applied Genetics*, 1, 327–341, 1982) containing the neomycin resistance gene Neo$^r$ and SV40 polyadenylation signals. The EcoRI and HindIII sites were then removed by restriction digesting, blunt ending with klenow polymerase, and religating. EcoRI and HindIII cloning sites were then inserted at the XhoI and SmaI sites of the polylinker by conventional techniques using EcoRI and HindIII linkers.

b) Cloning of subunit cDNAs into pMSGneo

Bovine $\alpha_1$ and $\beta_1$ GABA$_A$ receptor cDNAs were obtained from the Molecular Neurobiology Unit, MRC Centre, Hills Road, Cambridge (Scholfield, P. et al. *Nature*, 328, 221–227, 1987). Bovine $\gamma_2$ cDNA was cloned by the method of Whiting, P. et al. (*Proc. Natl. Acad. Sci. USA*, 87, 9966–9970, 1990). Bovine $\alpha_1$ was subcloned from pbGR$\alpha$sense by digestion with EcoRI, blunt ending the DNA with klenow polymerase, addition of HindIII linkers by ligation, digestion with HindIII and ligation into the HindIII site of pMSGneo. Bovine $\beta_1$ was subcloned from pbGR$\beta$sense by restriction digestion with EcoRI (partial digestion), klenow polymerase blunt ending, ligation of HindIII linkers, restriction digestion with HindIII and ligation into HindIII site of pMSGneo. Before subcloning into pMSGneo, the bovine $\gamma_2$ cDNA was modified from the published sequence as follows. The 5' untranslated region of the bovine $\alpha_1$ cDNA (bases 60–200 of the published sequence) was added to the 5' end of the published $\gamma_2$ sequence by amplifying the $\alpha_1$ untranslated region using polymerase chain reaction, and then subcloning the product into the 5' BamHI (site in the polylinker of the Bluescript Sk$^-$ cloning vector; Bluescript vector purchased from Stratagene, San Diego, U.S.A.) HindIII sites of the $\gamma_2$ cDNA. The modified $\gamma_2$ cDNA was then subcloned into pMSGneo by digestion with XbaI (site in the polylinker of the cloning vector), blunt ending with klenow polymerase, ligation of XhoI linkers, digestion with XhoI (site in the polylinker of the cloning vector), and ligation into XhoI site of pMSGneo.

c) Co-transfection of mouse Ltk$^-$ cells

Ltk$^-$ cells were obtained from the Salk Institute for Biological Studies, San Diego, Calif. Cells were grown at 37° C., 5–8% $CO_2$, in Modified Eagles Medium containing penicillin, streptomycin and 10% fetal calf serum. The expression vector harbouring the GABA$_A$ receptor subunit DNAs for co-transfection was prepared by a standard protocol (Chen, C. and Okayama, H., *BioTechniques*, 6, 632–638, 1988). For co-transfection, Ltk$^-$ cells were plated in dishes (approx. $2\times10^5$ cells/dish) and grown overnight. The transfection was performed by calcium phosphate precipitation using a kit (purchased from 5 Prime→3 Prime Products, Westchester, Pa.). Co-transfection was performed according to manufacturers' instructions, using 5 µg of each subunit DNA construct per 10 cm dish of cells. After 2 days in culture the cells were divided 1:8 into culture medium containing 1 mg/ml neomycin [Geneticin (obtainable from Gibco BRL, Paisley, Scotland, U.K.)]. After a further week the concentration was increased to 1.5 mg/ml, and then 2 mg/ml 1 week after that. Resistant clones of cells were isolated and subcloned using cloning cylinders. Subclones were analysed using radioligand binding: subclones were grown in 10 cm culture dishes, and when confluent changed into culture medium containing 1 µM dexamethasone (obtainable from Sigma Chemical Company, Poole, Dorset, United Kingdom). 3–5 days later the cells were harvested, membranes prepared and used for radioligand binding (see Example 2, step (a) below) using the benzodiazepine antagonist $^3$H Ro15-1788 (obtained from New England Nuclear, Du Pont (U.K.) Ltd, Stevenage, United Kingdom). The clone expressing the highest amount of $^3$H Ro15-1788 binding was subcloned from a single cell by limiting dilution. The resultant clonal population of cells described below is referred to as population A.

EXAMPLE 2

CHARACTERIZATION OF $\alpha_1\beta_1\gamma_{2L}$ TRANSFECTED CELLS a) Radioligand binding The nature of the recombinant $\alpha_1\beta_1\gamma_{2L}$ GABA$_A$ receptors prepared as described in Example 1 was addressed by characterization of the benzodiazepine (BZ) binding pharmacology, using the BZ antagonist $^3$H Ro15-1788. For radioligand binding assays, cells which had been induced by culture in dexamethasone containing medium for 3–5 days were scraped off into 50 mM Tris, pH7.5, 100 mM NaCl in the form of Tris buffered saline (TBS) and pelleted (20,000 rpm, Sorvall RC5C centrifuge). The cell pellet was resuspended in 50 mM Tris, pH7.5, homogenised using an Ultra-Turrax homogeniser and then pelleted as above. This was repeated once more, and the cells then resuspended in TBS (0.4 ml per original 10 cm dish of cells). Radioligand binding was performed in 0.1 ml final volume TBS, containing 5–15 fmols of $^3$H Ro15-1788 binding sites. After 1 hour incubation on ice the membranes were harvested onto filters using a Brandel cell harvester, washed with cold TBS, and bound radioactivity determined by scintillation counting. The recombinant $\alpha_1\beta_1\gamma_{2L}$ receptors bound $^3$H Ro15-1788 with high affinity ($K_D$0.4 nM), at levels of up to 200 fmols/10 cm dish of cells. No binding was seen to either untransfected Ltk$^-$ cells, or population A cells which had not been induced by addition of dexamethasone to the culture medium, confirming that the $^3$H Ro15-1788 was binding to recombinant $\alpha_1\beta_1\gamma_2$ GABA$_A$ receptors. The $^3$H Ro15-1788 binding was inhibited by flunitrazepam, CL218872, FG8205, $\beta$CCM, zolpidem and Ro15-4513, confirming the BZ pharmacology of the recombinant receptor. Since it is established that only GABA$_A$ receptors containing an $\alpha$, a $\beta$ and a $\gamma$ subunit exhibit BZ binding (Pritchett, D. et al., *Nature*, 338, 582–585, 1989) these data confirm the nature of the recombinant $\alpha_1\beta_1\gamma_2$ GABA$_A$ receptors expressed by population A cells.

b) Electrophysiology

The nature of the GABA$_A$ receptor expressed by population A cells has been extensively characterised by electrophysiological techniques, using whole cell patch clamp. Only cells induced by culture in the presence of dexamethasone showed responses to GABA. Concentration response curves to GABA gave a log EC$_{50}$ of 5.2, and a Hill coefficient of 1.9. The response to GABA was potentiated by BZs flunitrazepam and CL218872, by the barbiturate pentobarbitone, and by the steroid alphaxalone. The response to GABA was antagonised by both bicuculline and picrotoxin. All these electrophysiological data confirm that the recombinant GABA$_A$ receptor expressed by population A cells has all of the properties expected of a bona fide GABA$_A$ receptor.

EXAMPLE 3

ISOLATION AND SEQUENCING OF cDNAS ENCODING HUMAN GABA$_A$ RECEPTOR $\alpha_2$, $\alpha_3$, $\alpha_5$, $\alpha_6$ & $\beta_2$ SUBUNITS a) cDNA libraries cDNAs were cloned from human foetal brain ($\alpha_2$, $\alpha_3$), hippocampal ($\alpha_5$, $\beta_2$) and cerebellum ($\alpha_6$) lambda bacteriophage cDNA libraries. All cDNA libraries were constructed in the lambdaZAP vector, and were purchased from Stratagene (San Diego, Calif.). For screening, the cDNA libraries were plated according to the manufacturer's instructions, at 40,000 pfu per 137 mm plate. Filter lifts were taken using Hybond N filters (Amersham) according to the manufacturer's instructions.

b) Isolation of cDNA encoding human $\alpha_2$ subunit

A bovine $\alpha_2$ cDNA (obtained from E. Barnard, Molecular Neurobiology, University of Cambridge, Hills Road, Cambridge; Levitan et al., Nature, 1988, 335, 76) was labelled to high specific activity (>1.10$^9$ cpm/µg) with $^{32}$P by random priming and used as a probe. Library filters (8 replica filters) were prehybridised for 3–6 hours at 42° C. in 5× SSPE (1× SSPE is 0.18M NaCl, 0.01M Na$_3$PO$_4$ [pH7.4], 1 mM EDTA), 5× Denhardt's solution, 100 µg/ml salmon sperm DNA, 0.1% sodium dodecyl sulphate (SDS), 30% formamide. Hybridisation was performed in the same buffer for 18 hours at 42° C., including 0.5–1.10$^6$ cpm $^{32}$P-labelled probe per ml of hybridisation buffer. Filters were washed at 55° C. in 5× SSPE (2× 15 minutes) and 1× SSPE (2× 15 minutes) and exposed to Kodak XAR film for 1–3 days. Positive clones were plaque purified using standard techniques, and the Bluescript plasmid (Stratagene) "rescued" according to manufacturer's instructions. cDNA clones were sequenced on both strands by standard techniques using Sequenase II enzyme (United States Biochemicals). The nucleotide sequence of the cDNA encoding the human GABA$_A$ receptor $\alpha_2$ subunit, together with the deduced amino acid sequence corresponding thereto, is shown in FIG. 2 of the accompanying drawings.

c) Isolation of cDNA encoding human $\alpha_3$ subunit

A bovine $\alpha_3$ cDNA (obtained from E. Barnard, Molecular Neurobiology, University of Cambridge, Hills Road, Cambridge; Levitan et al., Nature, 1988, 335, 76) was labelled to high specific activity with $^{32}$P by random priming and used as a probe. Library filters were prehybridised for 3–6 hours at 55° C. in 5× SSPE, 5× Denhardt's solution, 0.1% SDS, 100 µg/ml salmon sperm DNA, and hybridised for 18 hours, 55° C. in the same buffer, containing 0.5–1×10$^6$ cpm/ml of $^{32}$P-labelled bovine $\alpha_3$ cDNA as probe. Filters were washed and exposed to X-ray film as described above; cDNA clones were rescued and sequenced as described above. The longest $\alpha_3$ cDNA clone was missing in approximately 100 bp of the 5' end of the coding region. This was obtained by PCR using as primers an oligonucleotide "anchor" primer derived from the T7 primer sequence of Bluescript vector (5'AGCGCGCGTAATACGACTCACTATAGGGCGAA3'; SEQ ID NO:11) and an oligonucleotide derived from sequence near the 5' end of the truncated $\alpha_3$ cDNA, containing an internal HpaI site (5'CAGCATGAATTGTTAACCTCATTGTA3'; SEQ ID NO:12). Oligonucleotides were synthesised on an Applied Biosystems 380B synthesiser. PCR was performed as described above, and a 300 bp PCR product obtained which was double digested with HpaI and KpnI and subcloned into the similarly cut truncated $\alpha_3$ cDNA to yield a full length human $\alpha_3$ cDNA. The cDNA was sequenced on both strands as described above. The nucleotide sequence of the cDNA encoding the human GABA$_A$ receptor $\alpha_3$ subunit, together with the deduced amino acid sequence corresponding thereto, is shown in FIG. 3 of the accompanying drawings.

d) Isolation of cDNA encoding human $\alpha_5$ subunit

A rat $\alpha_5$ cDNA obtained by polymerase chain reaction (PCR) was used as a probe to screen the cDNA library. For PCR, sequences of the oligonucleotide primers were taken from the published $\alpha_5$ sequences (Khrestchatisky et al., Neuron, 1989, 3, 745) and incorporated a Hind III site for subcloning purposes: 5'ATTATTCAAGCTTGCCATGGACAATGGAATGCTC3' [SEQ ID NO:13] (bp114–148); 5'GGTTTCCAGCTTACTTTGGAGAGGTAGC3'[SEQ ID NO;14] (bp1507–1535). PCR and subcloning of the PCR product into Bluescript SK-vector (Stratagene) for analysis was performed as described elsewhere (Whiting et al., Proc. Natl. Acad. Sci. USA, 1990, 87, 9966) except that rat brain cDNA was used as template. The rat $\alpha_5$ cDNA was labelled with $^{32}$P and used to screen the human hippocampal cDNA library, and positive $\alpha_5$ clones rescued and sequenced as described for $\alpha_2$ above. The nucleotide sequence of the cDNA encoding the human GABA$_A$ receptor $\alpha_5$ subunit, together with the deduced amino acid sequence corresponding thereto, is shown in FIG. 4 of the accompanying drawings.

e) Isolation of cDNA encoding human $\alpha_6$ subunit

A rat $\alpha_6$ cDNA obtained by PCR was used as a probe to screen the cDNA library. PCR was performed as described above for $\alpha_5$, using oligonucleotide primers derived from the published rat $\alpha_6$ sequence (Luddens et al., Nature, 1990, 346, 648) incorporating an EcoRI site for subcloning purposes: 5'GAGGAAGAATTCAGGAGGGTGACCT3'[SEQ ID NO:15] (bp48–72); 5'GAAAATAACGAATTCCAGTGTCCAGCTTT3'[SEQ ID NO:16] (bp1376–1404). The rat $\alpha_6$ cDNA clone isolated by PCR was labelled with $^{32}$P and used to screen a human cerebellum cDNA library, as described above for $\alpha_2$. Positive $\alpha_6$ clones were purified, rescued and sequenced as described above. None of the cDNAs contained a complete coding region. To obtain a full length cDNA 3 clones were joined together using convenient restriction sites. The nucleotide sequence of the cDNA encoding the human GABA$_A$ receptor $\alpha_6$ subunit, together with the deduced amino acid sequence corresponding thereto, is shown in FIG. 5 of the accompanying drawings.

f) Isolation of cDNA encoding human $\alpha_2$ subunit

Human $\beta_2$ cDNA was isolated using as a probe a short human $\beta_2$ cDNA obtained by PCR. PCR was performed as described above (except that the human cerebellum cDNA library was used as template), using oligonucleotide primers derived from the published rat $\beta_2$ sequence (Ymer et al., EMBO J., 1989, 8, 1665), incorporating EcoRI sites for subcloning purposes: 5'CAAAAGAATTCAGCTGAGAAAGCTGCTAATGC3' [SEQ ID NO:17] (bp1088–1119); 5'TCAGGCGAATTCTCTTTTGTGCCACATGTCGTTC3' [SEQ ID NO:18] (bp1331–1364). The human $\beta_2$ clone obtained by PCR was radiolabelled with $^{32}$P and used to screen a human hippocampal cDNA library, as described above for $\alpha_2$. The largest cDNA clone obtained lacked the 5' 500 bp of the coding region of the $\beta_2$ subunit. This was obtained by PCR using as primers an oligonucleotide "anchor" primer derived from the T7 primer sequence of the Bluescript vector (5'AGCGCGCGTAATACGACTCACTATAGGGCGAA3'; SEQ ID NO:19), and an oligonucleotide derived from sequence near the 5' end of the truncated $\beta_2$ cDNA, containing a KpnI site (5'CATCCAGTGGGTACCTCCTTAGGT3'; SEQ ID NO:20). PCR was performed as described above, and a 700 bp PCR product obtained which was digested with kpnI and subcloned into the truncated cDNA clone (also KpnI digested) to yield a full length human $\beta_2$ cDNA. The nucleotide sequence of the cDNA encoding the human GABA$_A$ receptor $\beta_2$ subunit, together with the deduced amino acid sequence corresponding thereto, is shown in FIG. 6 of the accompanying drawings.

EXAMPLE 4

PREPARATION OF STABLY TRANSFECTED CELLS EXPRESSING $\alpha_1\beta_3\gamma_{2S}$, $\alpha_2\beta_3\gamma_{2S}$ AND $\alpha_5\beta_3\gamma_{2S}$ SUBUNIT COMBINATIONS OF THE HUMAN $GABA_A$ RECEPTOR Isolation and sequence of human $\alpha_2$ and $\alpha_5$ cDNAs have been described in Example 3. The sequence of human $\alpha_1$ cDNA has been published previously by Schofield et al., *FEBS Lett.*, 1989, 244, 361. It differs from the bovine sequence at a single amino acid (trp95 in bovine $\alpha_1$; arg in human $\alpha_1$). To create a human $\alpha_1$ cDNA the bovine sequence was converted to the human by site directed mutagenesis of amino acid 95 with the oligonucleotide 5'GCAATGAAAATCCGGACTGGCAT3'; SEQ ID NO:21), using methods described elsewhere (K. Wafford and P. Whiting, *FEBS Lett.*, 1992, 313, 113–117). The sequence of human $\gamma_2$ has been published previously by Pritchett et al., *Nature*, 1989, 338, 582. A human $\gamma_2$ cDNA was isolated by PCR using conditions described elsewhere (Whiting et al., *Proc. Natl. Acad. Sci. USA*, 1990, 87, 9966–9970), using human hippocampal cDNA library as template and oligonucleotide primers derived from the 5' and 3' untranslated regions of the published $\gamma_2$ sequence, incorporating a Hind III restriction site:

5'GGGAGGGAAGCTTCTGCAACCAAGAGGC3'; SEQ ID NO:22),

5'ACCACATAGAAGCTTATTTAAGTGGAC3'; SEQ ID NO:23). Sequencing indicated that the form of $\gamma_2$ used is the short form, $\gamma_{2S}$, lacking the 24 bp insert in the putative cytoplasmic loop region (Whiting et al., *Proc. Natl. Acad. Sci. USA*, 1990, 87, 9966–9970). The sequence of human $\beta_3$ has been published by Wagstaff et al., *Am. J. Hum. Genet.*, 1991, 41, 330–337. A human $\beta_3$ cDNA was isolated by screening a human foetal brain cDNA library (see Example 3) with a short human $\beta_3$ cDNA probe encoding the putative cytoplasmic loop domain which had been obtained using PCR.

Human $\alpha_1$, $\alpha_2$, $\alpha_5$, $\beta_3$ and $\gamma_{2S}$ cDNAs were subcloned into the eukaryotic expression vector pMSGneo (see Example 1) using standard techniques (cf. Maniatis et al. in *Molecular Cloning, A Laboratory Manual*, Cold Spring Harbor Press, New York, 2nd Edition, 1989) and stable cell lines expressing human $\alpha_1\beta_3\gamma_{2S}$, $\alpha_2\beta_3\gamma_{2S}$ and $\alpha_5\beta_3\gamma_{2S}$ $GABA_A$ receptors were established as described in Example 1.

EXAMPLE 5

PREPARATION OF STABLY TRANSFECTED CELLS EXPRESSING $\alpha_1\beta_1\gamma_{2S}$, $\alpha_1\beta_2\gamma_{2S}$, $\alpha_3\beta_3\gamma_{2S}$ AND $\alpha_6\beta_3\gamma_{2S}$ SUBUNIT COMBINATIONS OF THE HUMAN $GABA_A$ RECEPTOR Isolation of $\alpha_3$ and $\alpha_6$ cDNAs is as described in Example 3, and isolation of $\alpha_1$, $\beta_3$ and $\gamma_{2S}$ cDNAs is as described above in Example 4. Human $\beta_1$ subunit cDNA was isolated by PCR from human brain cDNA as described above. Oligonucleotide primers used for the PCR were derived from the published human $\beta_1$ sequence (Schofield et al., *FEBS Lett.*, 1989, 244, 361–364). 5' and 3' untranslated regions incorporating Hind III restriction enzyme sites for subcloning:

5'TAATCAAGCTTAGTAATGTGGACAGTACAAAAT3'; SEQ ID NO:24) and

5'AAATGGAAGCTTTAGAACAGACCTCAGTGTACA3'; SEQ ID NO:25). Human $\alpha_1$, $\alpha_3$, $\alpha_6$, $\beta_1$, $\beta_2$, $\beta_3$ and $\gamma_{2S}$ cDNAs were subcloned into the eukaryotic expression vector pMSGneo (see Example 1) using standard techniques (cf. Maniatis et al. in *Molecular Cloning, A Laboratory Manual*, Cold Spring Harbor Press, New York, 2nd Edition, 1989) and stable cell lines expressing human $\alpha_1\beta_1\gamma_{2S}$, $\alpha_1\beta_2\gamma_{2S}$, $\alpha_3\beta_3\gamma_{2S}$ and $\alpha_6\beta_3\gamma_{2S}$ $GABA_A$ receptors were established as described in Example 1.

---

We claim:

1. A rodent fibroblast cell line stably co-transfected with DNA expressing a human $GABA_A$ receptor comprising the $\alpha_1\beta_3\gamma_2$ subunit combination.

2. A cell line of claim 1 which is a mouse fibroblast Ltk⁻ cell line.

3. A rodent fibroblast cell line stably co-transfected with DNA expressing a human $GABA_A$ receptor comprising the $\alpha_2\beta_3\gamma_2$ subunit combination.

4. A cell line of claim 3 which is a mouse fibroblast Ltk⁻ cell line.

5. A rodent fibroblast cell line stably co-transfected with DNA expressing a human $GABA_A$ receptor comprising the $\alpha_5\beta_3\gamma_2$ subunit combination.

6. A cell line of claim 5 which is a mouse fibroblast Ltk⁻ cell line.

7. A rodent fibroblast cell line stably co-transfected with DNA expressing a human $GABA_A$ receptor comprising the $\alpha_1\beta_1\gamma_{2S}$ subunit combination.

8. A cell line of claim 7 which is a mouse fibroblast Ltk⁻ cell line.

9. A rodent fibroblast cell line stably co-transfected with DNA expressing a human $GABA_A$ receptor comprising the $\alpha_1\beta_2\gamma_2$ subunit combination.

10. A cell line of claim 9 which is a mouse fibroblast Ltk⁻ cell line.

11. A rodent fibroblast cell line stably co-transfected with DNA expressing a human $GABA_A$ receptor comprising the $\alpha_3\beta_3\gamma_2$ subunit combination.

12. A cell line of claim 11 which is a mouse fibroblast Ltk⁻ cell line.

13. A rodent fibroblast cell line stably co-transfected with DNA expressing a human $GABA_A$ receptor comprising the $\alpha_6\beta_3\gamma_2$ subunit combination.

14. A cell line of claim 13 which is a mouse fibroblast Ltk⁻ cell line.

15. A membrane preparation derived from a rodent fibroblast cell line stably co-transfected with DNA expressing a human $GABA_A$ receptor wherein said human $GABA_A$ receptor is comprised of a subunit combination selected from a group consisting of $\alpha_1\beta_3\delta\gamma_2$, $\alpha_2\beta_3\delta\gamma_2$, and $\alpha_5\beta_3\delta\gamma_2$.

16. A preparation as claimed in claim 15 containing a human $GABA_A$ receptor consisting of the $\alpha_1\beta_3\gamma_{2S}$, $\alpha_2\beta_3\gamma_{2S}$ or $\alpha_5\beta_3\gamma_{2S}$ subunit combination isolated from stably co-transfected mouse Ltk⁻ fibroblast cells.

17. The membrane preparation of claim 15 wherein said rodent fibroblast cell line is a mouse fibroblast Ltk⁻ cell line.

18. A membrane preparation derived from a rodent fibroblast cell line stably co-transfected with DNA expressing a human $GABA_A$ receptor wherein said human $GABA_A$ receptor is comprised of a subunit combination selected from a group consisting of $\alpha_1\beta_1\gamma_{2S}$, $\alpha_1\beta_2\gamma_2$, $\alpha_3\beta_3\gamma_2$, and $\alpha_6\beta_3\gamma_2$.

19. A preparation as claimed in claim 18 containing a human $GABA_A$ receptor consisting of the $\alpha_1\beta_1\gamma_{2S}$, $\alpha_1\beta_2\gamma_{2S}$, $\alpha_3\beta_3\gamma_{2S}$ or $\alpha_6\beta_3\gamma_{2S}$ subunit combination isolated from stably co-transfected mouse Ltk⁻ fibroblast cells.

20. The membrane preparation of claim 18 wherein said rodent fibroblast cell line is a mouse fibroblast Ltk⁻ cell line.

21. A method of screening for and designing a medicament which interacts with the human $GABA_A$ receptor, which comprises:

a) expressing a human recombinant $GABA_A$ receptor complex within a rodent fibroblast cell line stably co-transfected with DNA expressing said recombinant human $GABA_A$ receptor wherein said recombinant human $GABA_A$ receptor comprises a subunit combination selected from the group consisting of $\alpha_1\beta_3\gamma_2$, $\alpha_2\beta_3\gamma_2$, $\alpha_5\beta_3\gamma_2$, $\alpha_1\beta_1\gamma_{2S}$, $\alpha_1\beta_2\gamma_2$, $\alpha_3\beta_3\gamma_2$, and $\alpha_6\beta_3\gamma_2$;

b) incubating said rodent fibroblast cell line with at least one chemical compound; and, c) measuring the effect of said compound on the biological activity of said recombinant human $GABA_A$ receptor.

22. The method of claim 21 wherein said rodent fibroblast cell line is a mouse fibroblast Ltk⁻ cell line.

23. A method of screening for and designing a medicament which interacts with the human $GABA_A$ receptor, which comprises:

a) expressing a human recombinant $GABA_A$ receptor complex within a rodent fibroblast cell line stably co-transfected with DNA expressing said recombinant human $GABA_A$ receptor wherein said recombinant human $GABA_A$ receptor comprises a subunit combination selected from the group consisting of $\alpha_1\beta_3\gamma_2$, $\alpha_2\beta_3\gamma_2$, $\alpha_5\beta_3\gamma_2$, $\alpha_1\beta_1\gamma_{2S}$, $\alpha_1\beta_2\gamma_2$, $\alpha_3\beta_3\gamma_2$, and $\alpha_6\beta_3\gamma_2$;

b) preparing a membrane fraction from said rodent fibroblast cell line;

c) incubating said rodent fibroblast cell line with at least one chemical compound; and, d) measuring the effect of said compound on the biological activity of said recombinant human $GABA_A$ receptor.

24. The method of claim 23 wherein said rodent fibroblast cell line is a mouse fibroblast Ltk⁻ cell line.

* * * * *